United States Patent [19]

Moyle et al.

[11] Patent Number: 5,708,141

[45] Date of Patent: Jan. 13, 1998

[54] NEUTROPHIL INHIBITORS

[75] Inventors: Matthew Moyle, Escondido; David L. Foster, San Diego; George P. Vlasuk, Carlsbad, all of Calif.

[73] Assignee: Corvas International, Inc., San Diego, Calif.

[21] Appl. No.: 249,041

[22] Filed: May 24, 1994

Related U.S. Application Data

[63] Continuation of Ser. No. 881,721, May 11, 1992, abandoned.

[51] Int. Cl.$^6$ .............................. C07K 2/00; A61K 35/56
[52] U.S. Cl. ..................... 530/350; 530/417; 424/520; 514/8
[58] Field of Search .............................. 424/85.1, 522, 424/527, 520; 514/2, 8; 530/351, 395, 350, 417; 435/69.1, 172.1, 172.3

[56] References Cited

U.S. PATENT DOCUMENTS

| | | | |
|---|---|---|---|
| 4,338,305 | 7/1982 | Corbin | 514/15 |
| 4,376,110 | 3/1983 | David et al. | 435/5 |
| 4,591,552 | 5/1986 | Neurath | 435/5 |
| 4,788,149 | 11/1988 | Cerami et al. | 435/212 |
| 4,797,277 | 1/1989 | Arfors | 435/1.2 |
| 4,840,793 | 6/1989 | Todd et al. | 424/153.1 |
| 4,855,231 | 8/1989 | Stroman et al. | 435/69.1 |
| 4,935,234 | 6/1990 | Todd et al. | 424/153.1 |
| 5,019,648 | 5/1991 | Schlossman et al. | 530/388.7 |
| 5,082,778 | 1/1992 | Overbeeke et al. | 435/172.3 |
| 5,147,637 | 9/1992 | Wright | 424/143.1 |
| 5,179,198 | 1/1993 | Okada et al. | 530/395 |

FOREIGN PATENT DOCUMENTS

| | | |
|---|---|---|
| 0289949 | 11/1988 | European Pat. Off. . |
| 0346078 | 12/1989 | European Pat. Off. . |
| 0438312 | 7/1991 | European Pat. Off. . |
| 0440351 | 8/1991 | European Pat. Off. . |
| 0507187 | 10/1992 | European Pat. Off. . |
| 0540128 | 5/1993 | European Pat. Off. . |
| 8900163 | 1/1989 | WIPO . |
| 9010453 | 9/1990 | WIPO . |
| 9211870 | 7/1992 | WIPO . |

OTHER PUBLICATIONS

E.L.V., Harris, et al., *Protein Purification Methods a Practical Approach*, (1989), pp. 1-4.
Suquet et al., 14 International Journal For Parasitology, 165 (1984).
Wadee et al., 44 Acta Tropica 343 (1987).
Leid et al., 9 Parasite Immunology 195 (1987).
Leid et al., 17 International Journal For Parasitology 1349 (1987).
Alkarmi et al., 69 Experimental Parasitology 16 (1989).
Bruschi et al., XXXV Wadomosci Parazytologiczne 391 (1989).
Bruschi et al., 76 J. Parasitology 577 (1990).
Shepherd et al., 44 Molecular & Biochemical Parasitology 81 (1991).

Alkarmi et al., "*Echinococcus multilocularis*: Inhibition of Murine Neutrophil and Macrophage Chemotaxis," *Experimental Parasitology* 69:16-22 (1989).
Amar et al., "K562 Cells Produce an Anti-Inflammatory Factor That Inhibits Neutrophil Functions In Vivo," *Blood* 80:1546-1552 (1992).
"Anti-Adhesion Therapy," *Adhesion: Its Role in Inflammatory Disease*, pp. 133-134, Harlan and Liu eds., W.H. Freeman and Company, New York, (1992).
Aruffo and Seed, "Molecular cloning of a CD28 cDNA by a high-efficiency COS cell expression system," *Proc. Natl. Acad. Sci. USA* 84:8573-8577 (1987).
Aruffo and Seed, "Molecular cloning of a two CD7 (T-cell leukemia antigen) cDNAs by a COS cell expression system," *The EMBO Journal* 6:3313-3316 (1987).
Balbas and Bolivar, "Design and Construction of Expression Plasmid Vectors in *Escherichia coli*," *Methods in Enzymology* 185:14-37 (1990).
Baron et al., "Elicitation of Peritoneal Polymorphonuclear Neutrophils From Mice," *Journal of Immunol. Methods* 49:305-313 (1982).
Barton et al., "The Effect of Anti-Intercellular Adhesion Molecule-1 on Phorbol-Ester-Induced Rabbit Lung Inflammation", *J. Immunology* 143:1278-1282 (1989).
Becker and Guarente, "High Efficiency Transformation of Yeast by Electroporation," *Methods in Enzymology* 194:182-187 (1991).
Beller et al., "Anti-Mac-I Selectively Inhibits the Mouse and Human Type Three Complement Receptor," *J. Exp. Med.* 156:1000-1009 (1982).
Bevilacqua et al., "Identification of an inducible endothelial-leukocyte adhesion molecule", *Proc. Natl. Acad. Sci. USA* 84:9238-9242 (1987).
Bruschi et al., "Inhibition of Leukocyte Function by Serum from Patients with Trichinellosis," *J. Parasitol.* 76:577-579 (1990).
Bruschi et al., "Modulating Effects By Trichinella Spiralis Sensu Stricto Excretory/Secretory Antigens of Human Neutrophil Functions," *Wiadomosci Parazytologizne* 35:391-399 (1989).
Burch et al., "N-(Fluorenyl-9-methoxycarbonyl) amino acids, a class of antiinflammatory agents with a different mechanism of action", *Proc. Natl. Acad. Sci. USA* 88:355-359 (1991).
Butterworth, "Cell-Mediated Damage to Helminths," *Advances in Parasitol.* 23:143-235 (1984).

(List continued on next page.)

*Primary Examiner*—John Ulm
*Assistant Examiner*—L. Spector
*Attorney, Agent, or Firm*—Lyon & Lyon LLP

[57] ABSTRACT

Compositions enriched for Neutrophil Inhibitory Factor which inhibit neutrophil activity including adhesion to vascular endothelial cells are provided. Such compositions may comprise a glycoprotein isolated from nematodes, particularly of the genus Ancylostoma. These compositions are useful in the therapy of conditions which involve abnormal or undesired inflammatory responses.

4 Claims, 6 Drawing Sheets

OTHER PUBLICATIONS

Buyon et al., "Dissociation Between Increased Surface Expression of Gp165/95 and Homotypic Neutrophil Aggregation", *J. Immunology* 140:3156–3160 (1988).

Camussi et al., "Antiinflammatory Peptides (Antiflammins) Inhibit Synthesis of Platelet–Activating Factor, Neutrophil Aggregation and Chemotaxis, and Intradermal Inflammatory Reactions", *J. Exp. Med.* 171:913–927 (1990).

Carlos et al., "Vascular Cell Adhesion Molecule–1 Mediates Lymphocyte Adherence to Cytokine–Activated Cultured human Endothelial Cells," *Blood* 76:965–970 (1990).

Carlos and Harlan, "Membrane Proteins Involved in Phagocyte Adherence to Endothelium," *Immunol. Rev.* 114:5–28 (1990).

Carrey, "Peptide Mapping," *Protein Structure A Practical Approach*, T.E. Creighton eds., IRL Press New York pp. 117–143 (1989).

Carroll et al., "The Anticoagulant Effects of the Hookworm, Ancylostoma ceylanicum: Observations on Human and Dog Blood In Vitro and Infected Dogs in Vivo," *Thromb Haemostas*, 51:222–227 (1984).

Chang et al., "Phenotypic expression in *E. coli* of a DNA sequence coding for mouse dihydrofolate reductase," *Nature* 275:617–624 (1978).

Clark et al., "Effects of In Vivo Prednisone on In Vitro Eosinophil and Neutrophil Adherence and Chemotaxis", *Blood* 53:633–641 (1979).

Clements et al, "Secretion of human epidermal growth factor from *Saccharomyces cerevisia* using synthetic leader sequences," *Gene* 106:267–272 (1991).

Dana et al., "Expression of a soluble and functional form of the human β2 integrin CD11b/CD18", *Proc. Natl. Acad. Sci. USA* 88:3106–3110 (1991).

Dehlawi and Wakelin, "Suppression of Mucoasal Mastocytosis by *Nematospiroides dubius* results from an adult worm–mediated effect upon host lymphocytes," *Parasite Imm.* 10:85–95 (1988).

Desser et al., "Guinea Pig Heterophil and Eosinophil Peroxidase," *Arch. Biochem. Biophys.* 148:452–465 (1972).

Diamond et al., "ICAM–1 (CD54): A Counter–Receptor for Mac–1 (CD11b/CD18)," *J. Cell Biol.* 111:3129–3139 (1990).

Dobrina et al., "Mechanism of Eosinophil Adherence to Cultured Vascular Endothelial Cells," *J. Clin. Invest.* 88:20–26 (1991).

Eiff, "Nature of an Anticoagulant From the Cephalic Glands of Ancylostoma Caninum," *J. Parasitology* 52:833–843 (1966).

Else and Wakelin, "Genetically–determined influences on the ability of poor responder mice to respond to immunization against *Trichuris muris*," *Parasitology* 100:479–489 (1990).

Evans et al., "Effect of Inhaled Corticosteroids on Peripheral Blood Eosinophil Counts and Density Profiles in Asthma," *J. Allergy Clin. Immunol.* 91:643–650 (1993).

Feldman et al., "Endocytosis by Macrophages of Altered Soluble Protein, The Effect of Binding to Particulate Surfaces and of IgM and IgG Antibody," *Journal of Immunology* 113:329–342 (1974).

Flavin et al., "Monoclonal Antibodies Against Intercellular Adhesion Molecule 1 Prolong Cardiac Allograft Survival in Cynomolgus Monkeys", *Transplantation Proceedings* 23:533–534 (1991).

Flower, "Lipocortin and the mechanism of action of the glucocorticoids, Eleventh Gaddum Memorial Lecture", *Eur. J. Pharmacol.* 94:987–1015 (1988).

Fuorets and Nathan, "Role of CD11/CD18 Integrins and cAMP in TNF–Induced Respiratory Burst of Human Neutrophils," *The Molecular Basis of Oxidative Damage by Leukocytes*, eds. Jesaitis, A.J. and Dratz, E.A., CRC Press, pp. 81–90 (1992).

Gasbarre et al., "Suppression of Antigen and Mitogen–Induced Proliferation of Bovine Lymphocytes by Excretory–Secretory Products of Oesophagostomum Radiatum," *Infection and Immunity* 48:540–545 (1985).

Geng et al., "Rapid neutrophil adhesion to activated endothelium mediated by GMP–140", *Nature* 343:757–760 (1990).

Gleich and Adolphson, "The Eosinophilic Leukocyte: Structure and Function," *Advances in Immunology* 39:177–253 (1986).

Gundel et al., "Endothelial Leukocyte Adhesion Molecule–1 Mediates Antigen–induced Acute Airway Inflammation and Late–phase Airway Obstruction in Monkeys", *J. Clin. Invest.* 88:1407–1411 (1991).

Hallgren,"Neutrophil and Eosinophil Involvement of the Small Bowel in Patients with Celiac Disease and Crohn's Disease: Studies on the Secretion Rate and immunohistochemical Localization of Granulocyte Granule Constituents," *Amer. J. Med.* 86:56–64 (1989).

Harlow and Lane, *Antibodies, A Laboratory Manual*, Cold Spring Harbor Laboratory, NY (1988) pp. 139–243.

Harlow and Lane, *Antibodies, A Laboratory Manual*, Cold Spring Harbor Laboratory, NY (1988) pp. 553–612.

Hermanek, "Nonspecific Immunomodulation Influences Resistance of Mice to Experimental Infection with *Mesocestoides corti* and *Ascaris suum*," *Journal of Helminthology* 65:121–132 (1991).

Horgan et al., "Antibody against leukocyte integrin (CD18) prevents reperfusion–induced lung vascular injury", *Am. Physiological Soc.*, pp. L315–L319 (1990).

Hynes, "Integrins: Versatility, Modulation, and Signaling in Cell Adhesion," *Cell* 69:11–25 (1992).

Insel, "Analgesic–Antipyretics and Antiinflamatory Agents: Drugs Employed in the Treatment of Rheumatoid Arthritis and Gout," *The Pharmacological Basis of Therapeutics*, Eds. Gilman et al., Pergamon NY, 8th ed. pp. 638–681 (1990).

Jendrisak et al., "Cloning cDNA into λgt10 and λgt11", *Methods in Enzymology* 152:359–371 (1987).

Jutila et al., "Function and Regulation of the Neutrophil MEL–14 Antigen in Vivo: Comparison with LFA–1 and MAC–1", *J. Immunology* 143:3318–3324 (1989).

Kanofsky et al., "Single Oxygen Production by Human Eosinophils," *J. Biol. Chem.* 263:9692–9696 (1988).

Keller, "Immune Reactions to *Nippostrongylus brasiliensis* in the Rat," *Int. Arch. Allergy* 37:197–215 (1970).

Keesey, "Glycoprotein processing inhibitors Bromoconduritol A/B," *Biochemica Information*, J. Keesey ed., Boehringer Mannheim Biochemical, Indianapolis, pp. 135–141 (1987).

Keesey, "General Tips on Enzymatic Digestion of Glycoproteins," *Biochemica information*, J. Keesey ed., Boehringer Mannheim Biochemical, Indianapolis, pp. 147–165 (1987).

Kikkawa et al., "The Type II Epithelial Cell of the Lung," *Laboratory Investigation*, 30:76–84 (1974).

Kishimoto et al., "The Leukocyte Integrins," *Adv. Immunol.* 46:149–182 (1989).

Klein, "Blood Cells and Their Origin," *Immunology, Blackwell Scientific Publications*, Boston pp. 8–28 (1990).

Knudsen et al., "Glucocorticoids Inhibit Transcriptional and Post-Transcriptional Expression of Interleukin 1 in U937 Cells", *J. Immunology* 139:4129–4134 (1987).

Kohler and Milstein, "Continuous Cultures of Fused Cells Secreting Antibody of Predefined Specificity," *Nature* 256:495–497 (1975).

Kohno, "Refolding of Recombinant Proteins," *Methods in Enzymology* 185:187–195 (1990).

Kozak, "Point Mutations Define a Sequence Flanking the AUG Initiator Codon That Modulates Translation by Eukaryotic Ribosomes," *Cell* 44:283–292 (1986).

Kriegler, "Eukaryotic Control Elements," *Gene Transfer and Expression, A Laboratory Manual*, W.H. Freeman and Co., NY, NY pp. 4–18 (1991).

Kriegler, "Expression Cloning," *Gene Transfer and Expression, A Laboratory Manual*, W.H. Freeman and Co., NY, NY pp. 114–135 (1991).

Laemmli, "Cleavage of Structural Proteins during the Assembly of the Head of Bacteriophage T4", *Nature* 227:680–686 (1970).

Lamas et al., "Studies on the Adhesive Interaction Between Purified Human Eosinophils and Cultured Vascular Endothelial Cells," *J. Immunol.* 140:1500–1505 (1988).

Larson and Springer, "Structure and Function of Leukocyte Integrins", *Immunology. Rev.* 114:181–217 (1990).

Leid, "Parasite Defense Mechanisms for Evasion of Host Attack: a Review," *Veterinary Parasitology* 25:147–162 (1987).

Leid et al., "Inhibition of Equine Neutrophil Chemotaxis and Chemokinesis by a *Taenia taeniaeformis* proteinase inhibitor, *taeniasestain*," *Parasite Immunology* 9:195–294 (1987).

Leid et al., "Inhibition of Neutrophil Aggregation By Taeniaestatin, A Cestode Proteinase Inhibitor," *Int'l J. Parasitol.* 17:1349–1353 (1987).

Lewinsohn et al., "Leukocyte-Endothelial Cell Recognition: Evidence of a Common Molecular Mechanism Shared by Neutrophils, Lymphocytes, and Other Leukocytes", *J. Immunology* 138:4313–4321 (1987).

Lowe et al., "ELAM-1-Dependent Cell Adhesion to Vascular Endothelium Determined by a Transfected Human Fucosyltransferase cDNA", *Cell* 63:475–484 (1990).

MacDonald et al., "Isolation of RNA Using Guanidinium Salts", *Methods in Enzymology* 152:219–227 (1987).

MacGregor, "Granulocyte Adherence Changes Induced by Hemodialysis, Endotoxin, Epinephrine, and Glucocorticoids", *Annals of Internal Medicine* 86:35–39 (1977).

Maizels et al. "Immunological Modulation and Evasion by Helminth Parasites in Human Populations," *Nature* 365:797–805 (1993).

Makoff and Smallwood, "The Use of Two-Cistron Constructions in Improving the Expression of a Heterologous Gene in *E. coli*," *Nucleic Acids Research* 18:1711–1718 (1990).

McCarron et al., "Methods for the Collection of Peritoneal and Alveolar Macrophages," *Methods in Enzymology*, 108:274–284 (1984).

McDonald et al., "Isolation of RNA Using Guanidinium Salts," *Meth. Enzymol.* 152:219–227 (1987).

Michishita et al.,"A Novel Divalent Cation-Binding Site in the A Domain of the $\beta2$ Integrin CR3 (CD11b/CD18) is Essential for Ligand Binding," *Cell* 72:857–867 (1993).

Mileski et al., "Inhibition of CD18-dependent neutrophil adherence reduces organ injury after hemorrhagic shock in primates", *Surgery* 108:206–212 (1990).

Monroy et al., "Low Molecular Weight Immunosuppressors Secreted by Adult Nematospiroides dubius," 19:125–127 (1989).

Morrisey, "Silver Stain for Proteins in Polyacrylamide Gels: A Modified Procedure with Enhanced Uniform Sensitivity," *Anal. Biochem*, 117:307–310 (1981).

Moser et al., "Migration of Primed Human Eosinophils Across Cytokine-Activates Endothelial Cell Monolayers," *Blood* 79:2937–2945 (1992).

Moser et al, "IL–4 Controls The Selective Endothelium-Driven Transmigration Eosinophils From Allergic Individuals," *J. Immunol.* 149:1432–1438 (1992).

Mulligan et al., "Role of Endothelial-Leukocyte Adhesion Molecule 1 (ELAM-1) in Neutrophil-mediated Lung Injury in Rats", *J. Clin. Invest.* 88:1396–1406 (1991).

Murray et al., "Construction and Use of a Dominant, Selectable Marker: a Harvey Sarcoma Virus-Dihydrofolate Reductase Chimera," *Molecular and Cellular Biology* 3:32–43 (1983).

Nathan and Sanchez, "Tumor Necrosis Factor and CD11/CD18 ($\beta2$) Integrins Act Synergistically to Lower cAMP in Human Neutrophils", *J. of Cell Biology* 111:2171–2181 (1990).

Neilson, "Failure to Vaccinate Lambs Against Haemonchus Contortus With Functional Metabolic Antigens Identified by Immunoelectrophoresis," *Int. J. for Parasitology*, Pergamon Press, 5:427–430 (1975).

Patel et al., "Oxygen Radicals Induce Human Endothelial Cells to Express GMP-140 and Bind Neutrophils", *J. Cell Biology* 112:749–759 (1991).

Pelly et al., "Suppressive Effect of a Chronic Helminth Infection, Schistosomiasis Mansoni, on the Vitro Responses of Spleen and Lymph Node Cells to the T Cell Mitogens Phytohemagglutinin and Concanavalin A," *Amer. Soc. for Micro.* 13:1176–1183 (1976).

Pentilla et al., "©Suppression of Early Immunity to Nemato-Spiroides Dubius In Mice by Selective Depletion of Neutrophils with Monoclonal Antibody," *Aust. J. Exp. Biol. Sci.*, (Pt. 5) 63:531–543 (1985).

Perin et al., "Structure of the 116–kDa Polypeptidfe of the Clathrin–coated Vesicle/Synaptic Vesicle Proton Pump," *J. Biol. Chem.* 266:3877–3881 (1991).

Petreccia et al., "Respiratory Burst of Normal Human Eosinophils," *J. Leukoc. Biol.* 41:283–288 (1987).

Phillips et al., "ELAM-1 Mediates Cell Adhesion by Recognition of a Carbohydrate Ligand, Sialyl-Le$^{2n}$, *Science* 250:1130–1132 (1990).

Pine and Huang, "An Improved Method to Obtain a large Number of Mutants in a Defined Region of DNA," *Methods in Enzymology* 154:415–431 (1987).

Pine and Huang, "An Improved method to Obtain a Large Number of Mutants in a Defined Region of DNA," *Recombinant DNA Meth.* 33:603–618 (1989).

Prieto et al.,"Molecules Mediating Adhesion of T and B Cells, Monocytes and Granulocytes to Vascular Endothelial Cells," *Immunology* 63:631–637 (1988).

Pritchard et al., "Analysis of the mechanism of Immunodepression Following Heterologous Antigenic Stimulation During Concurrent Infection With *Nematospiroides dubius*," *Immunology* 51:633–642 (1984).

*Protein Purification Methods: A Practical Approach*, Harris and Angal eds., IRL Press at Oxford University Press, New York, 1989 pp. 1–4.

Ramos et al., "The Elevated Natural Killer Sensitivity of Targets Carrying Surface–Attached C3 Fragments Require the Availability of the iC3b Receptor (CR3) on the Effectors," *J. Immunol.* 140:1239–1243 (1988).

Ribeiro et al., "Role of Saliva in Blood–Feeding By Arthropods," *Ann. Rev. Entomol.* 32:463–478 (1987).

Ribeiro et al., "Antihemostatic, Antiinflammatory and Immunosuppressive Properties of the Saliva of a Tick, Ixodes Dammini," *J. Exp. Med.* 161:332–344 (1985).

Ribeiro et al., "Saliva of the Tick *Ixodes dammini* Inhibits Neutrophil Function", *Exp. Parasitol.* 70:382–388 (1990).

Rice et al., "Inducible Cell Adhesion Molecule 110 (INCAM–110) is an Endothelial Receptor for Lymphocytes," *J. Exp. Med.* 171:1369–1374 (1990).

Rodrick et al., "Effects of Supernatants of Polymorphonuclear Neutrophils Recruited by Different Inflammatory Substances on Mitogen Responses of Lymphocytes," *Inflammation* 6:1–11 (1982).

Rothlein et al., "A Human Intercellular Adhesion Molecule (ICAM–1) Distinct from LFA–1", *J. Immunology* 137:1270–1274 (1986).

Sambrook et al., *Molecular Cloning, a Laboratory Manual*, Cold Spring Harbor Laboratory Press, pp. A.1 (1989).

Sambrook et al., *Molecular Cloning, a Laboratory Manual*, Cold Spring Harbor Laboratory Press, pp. 1.33 (1989).

Sambrook et al., *Molecular Cloning, a Laboratory Manual*, Cold Spring Harbor Laboratory Press, pp. 1.74–1.84 (1989).

Sambrook et al., *Molecular Cloning, a Laboratory Manual*, Cold Spring Harbor Laboratory Press, pp. 1.85–1.86 (1989).

Sanger et al., "DNA sequencing with chain–terminating inhibitors", *Proc. Natl. Acad. Sci. USA* 74:5463–5467 (1977).

Savin et al., "Characterization, Cloning and Host–Protective Activity of a 30–Kilodalton Glycoprotein Secreted By the Parasitic Stages of Trichostrongylus Colubriformis," *Molecular and Biochemical Parasitology* 41:167–176 (1990).

Scarborough et al., "Barbourin, A GPIIb–IIIa–Specific Integrin Antagonist From the Venom of Sistrurus M. Barbouri," *J. Biol. Chem.* 266:9359–9362 (1991).

Schoner et al., "Role of mRNA translational efficiency in bovine growth hormone expression in *Escherichia coli*," *Proc. Natl. Acad. Sci. USA* 81:5403–5407 (1984).

Schroff et al., "Human Anti–Murine Immunoglobulin Responses in Patients Receiving Monoclonal Antibody Therapy", *Cancer Res.* 45:879–885 (1985).

Scowden et al., "Overwhelming Strongyloidiasis," *Medicine* 57:527–544 (1978).

Seed and Aruffo, "Molecular cloning of the CD2 antigen, the T–cell erythrocyte receptor, by a rapid immunoselection procedure," *Proc. Natl. Acad. Sci. USA* 84:3365–3369 (1987).

Shappell et al., "Mac–1 (CD11b/DC18) Mediates Adherence–Dependent Hydrogen Peroxide Production by Human and Canine Neutrophils," *J. Immunol.* 144:2702–2711 (1990).

Shepherd et al., "A Protein Secreted In Vivo by Echinococcus Granulosus Inhibits Elastase Activity and Neutrophil Chemotaxis," *Mol. Biochem. Parasitol.* 44:81–90 (1991).

Showell and Williams, "The Neutrophil in Inflammation," *Immunopharmacology*, eds. Gilman and Rogers, Telford Press, NJ pp. 23–63 (1989).

Smith et al., "Cooperative Interactions of LFA–1 and Mac–1 with Intercellular Adhesion Molecule–1 in Facilitating Adherence and Transendothelial Migration of Human Neutrophils in Vitro," *J. Clin. Invest.* 83:2008–2017 (1989).

Soule et al. "Membrane 126–kilodalton phosphoglycoprotein associated with human carcinomas identified by a hybridoma antibody to mammary carcinoma cells," *Proc. Natl. Acad. Sci. USA* 80:1332–1336 (1983).

Soulsby, "The evasion of the immune response and immunological unresponsiveness: parasitic helminth infections", *Immunol. Lett.* 16:315–320 (1987).

Spanjaard et al., "Expression of the rat interferon–$\alpha_1$ gene in *Escherichia coli* controlled by the secondary structure of the translation–initiation region," *Gene* 80:345–351 (1989).

Spellmann and Nossel, "Anticoagulant activity of dog hookworm," *American J. of Phys.* 220:922–927 (1971).

Stanssens et al., "Efficient Oligonucleotide–Directed Construction of Mutations in Expression Vectors by the Gapped Duplex DNA method using Alternating Selectable Markers," *Nucleic Acids Research* 17:4441–4454 (1989).

Staunton et al., "Primary Structure of ICAM–1 Demonstrates Interaction between Members of the Immunoglobulin and Integrin Supergene Families", *Cell* 52:925–933 (1988).

Staunton et al., "Functional cloning of ICAM–2, a cell adhesion ligand for LFA–1 homologous to ICAM–1", *Nature* 339:61–64 (1989).

Suquet et al., "Isolation and Partial Characterization of a Taenia Taeniaeformis Metacestode Proteinase Inhibitor," *Int'l J. Parasitol.* 14:165–172 (1984).

Thomas et al., "Inhibition of Neutrophil (PMN) Adherence by Anti–CD18 Monoclonal Antibody (mAb) Affects Resuscitation From Endotoxic Shock," *FASEB J.*, 5:A509 (1991).

Tiemeyer et al., "Carbohydrate ligands for endothelial–leukocyte adhesion molecule 1", *Proc. Natl. Acad. Sci. USA* 88:1138–1142 (1991).

Towbin et al., "Electrophoretic transfer of proteins from polyacrylamide gels to nitrocellulose sheets: Procedure and some applications," *Proc. Natl. Acad. Sci. USA* 76:4350–4354 (1979).

Tsuda et al., "Eosinophil Involvement in Atopic Dermatitis as Reflected by Elevated Serum Levels of Eosinophil Cationic Protein," *J. Dermatol.* 19:208–213 (1992).

Tuomanen et al., "Reduction of Inflammation, Tissue Damage, and Mortality in Bacterial Meningitis in Rabbits Treated with Monoclonal Antibodies Against Adhesion–Promoting Receptors of Leukocytes", *J. Exp. Med.* 170:959–968 (1989).

Vedder and Harlan, "Increased Surface Expression of CD11b/CD18 (Mac–1) Is Not Required for Stimulated Neutrophil Adherence to Cultured Endothelium", *J. Clin. Invest.* 81:676–682 (1988).

Vedder et al., "Inhibition of leukocyte adherence by anti–CD18 monoclonal antibody attenuates reperfusion injury in the rabbit ear", *Proc. Natl. Acad. Sci. USA* 87:2643–2646 (1990).

Von Asmuth et al., "Involvement of CD11b/CD18 Integrin, But Not of the Endothelial Cell Adhesion Molecules ELAM–1 and ICAM–1 in Tumor Necrosis Factor–$\alpha$–Induced Neutrophil Toxicity," *J. Immunol.* 147:3869–3875 (1991).

Wadee et al., "Characterization of Immunosuppressive Proteins of Brugia Malayi Microfilariae," *Acta Tropica* 44:343–352 (1987).

Wallace et al., "A Monoclonal Antibody Against the CD18 Leukocyte Adhesion Molecule Prevents Indomethacin–Induced Gastric Damage in the Rabbit", *Gastroenterology* 100:878–883 (1991).

Wallis et al., "Monoclonal Antibody–Defined Functional Epitopes on the Adhesion–Promoting Glycoprotein Complex (CDw18) of Human Neutrophils," *Blood* 67:1007–1013 (1986).

Walsh et al., "IL–5 enhances the in vitro adhesion of human eosinophils, but not neutrophils, in a leucocyte integrin (CD11/18)–dependent manner," *Immunology* 71:258–265 (1990).

Walz et al., "Recognition by ELAM-1 of the Sialyl-Le$^x$ Determinant on Myeloid and Tumor Cells", *Science* 250:1132–1135 (1990).

Watson et al., "Neutrophil influx into an inflammatory site inhibited by a soluble homing receptor–IgG chimaera", *Nature* 349:164–167 (1991).

Wegner et al., "Intercellular Adhesion Molecule–1 (ICAM–1) in the Pathogenesis of Asthma," *Science* 247:456–459 (1990).

Wiggin and Gibbs, "Studies of the immunomodulatory effects of low–level infection with *Ostertagia ostertagi* in calves," *Amer. J. Vet. Res.* 50:1764–1770 (1989).

Wiggin and Gibbs, "Adverse Immune Reactions and the Pathogenesis of Ostertagia Ostertagi Infections in Calves," *Amer. J. Vet. Res.* 51:825–832 (1990).

Winquist et al., "An Anti–CD18 MAb Limits Infarct Size in Primates Following Myocardial Ischemia and Reperfusion", Abstracts of the 63rd Scientific Sessions, III–70 at abstract 2785 (1990).

Zell et al., "DNA mismatch–repair in *Escherichia coli* counteracting the hydrolytic deamination of 5–methyl–cystosine residues," *EBMO J.* 6:1809–1815 (1987).

M. Moyle et al., J. Biol. Chem. 269(13):10008–15, Apr. 1 1994.

E.J.L. Souls by Immunol Letters vol. 16, issued 1987, pp. 315–320.

Harlow et al Antibodies : A Laboratory manual published 1988 by Cold Spring Harbor Laboratory pp. 72–77,92–97 128–135 & 141–157.

NEUTROPHIL INHIBITORS

This application is a continuation of application Ser. No. 07/881,721, filed May 11, 1992 now abandoned.

FIELD OF THE INVENTION

This invention relates to factors which inhibit neutrophil activity, including inhibition of neutrophil activation and adhesion of neutrophils to vascular endothelial cells.

BACKGROUND OF THE INVENTION

Neutrophils are a class of white blood cells (leukocytes) that comprise an essential component of the host defense system against microbial invasion. In response to soluble inflammatory mediators released by cells at the site of injury, neutrophils emigrate into tissue from the bloodstream by crossing the blood vessel wall. At the site of injury, activated neutrophils kill foreign cells by phagocytosis and by the release of cytotoxic compounds, such as oxidants, proteases and cytokines. Despite their importance in fighting infection, neutrophils themselves can promote tissue damage. During an abnormal inflammatory response, neutrophils can cause significant tissue damage by releasing toxic substances at the vascular wall or in uninjured tissue. Alternatively, neutrophils that stick to the capillary wall or clump in venules may produce tissue damage by ischemia. Such abnormal inflammatory responses have been implicated in the pathogenesis of a variety of clinical disorders including adult respiratory distress syndrome (ARDS); ischemia-reperfusion injury following myocardial infarction, shock, stroke, and organ transplantation; acute and chronic allograft rejection; vasculitis; sepsis; rheumatoid arthritis; and inflammatory skin diseases (Harlan et al., 1990 Immunol. Rev. 114, 5).

Neutrophil adhesion at the site of inflammation involves at least two discrete cell-cell interactive events. Initially, vascular endothelium adjacent to inflamed tissue becomes sticky for neutrophils; neutrophils interact with the endothelium via low affinity adhesive mechanisms in a process known as "rolling". In the second adhesive step, rolling neutrophils bind more tightly to vascular endothelial cells and migrate from the blood vessel into the tissue.

Neutrophil rolling along affected vascular segments and other initial low affinity contacts between neutrophils and the endothelium are mediated by a group of monomeric, integral membrane glycoproteins termed selectins. All three of the selectins so far identified, that is L-selectin (LECAM-1, LAM-1) present on the surface of neutrophils, E-selectin (endothelial leukocyte adhesion molecule-1; ELAM-1) present on endothelial cells and P-selectin (granule membrane protein-140, GMP-140; platelet activation-dependent granule-external membrane protein, PADGEM; CD62) expressed on endothelial cells, have been implicated in neutrophil adhesion to the vascular endothelium (Jutila et al., 1989 J. Immunol 143, 3318; Watson et al., 1991 Nature 349, 164; Mulligan et al., J. Clin. Invest. 88, 1396; Gundel et al., 1991 J. Clin. Invest. 88, 1407; Geng et al., 1990 Nature 343, 757; Patel et al., 1991 J. Cell Biol. 112, 749). The counter-receptor for E-selectin is reported to be the sialylated Lewis X antigen (sialyl-Lewis$^x$) that is present on cell-surface glycoproteins (Phillips et al., 1990 Science 250, 1130; Walz et al., 1990 Science 250, 1132; Tiemeyer et al., 1991 Proc. Natl. Acad. Sci.(U.S.A.) 88, 1138; Lowe et al., 1990 Cell 63, 475). Receptors for the other selectins are also thought to be carbohydrate in nature but remain to be elucidated.

The more stable secondary contacts between neutrophils and endothelial cells are mediated by a class of cell adhesion molecules known as integrins. Integrins comprise a broad range of evolutionarily conserved heterodimeric transmembrane glycoprotein complexes that are present on virtually all cell types. Members of the leukocyte-specific $\beta_2$ (CD18) family of integrins, which include $\alpha_L\beta_2$ (LFA-1) and $\alpha_M\beta_2$ (Mac-1; Mo-1; CR3) have been reported to mediate neutrophil adhesion to the endothelium (reviewed in Larson and Springer, 1990 Immunol Rev. 114, 181). Endothelial cell counter-receptors for these integrins are the intercellular cell adhesion molecules ICAM-1 and ICAM-2 for $\alpha_L\beta_2$ and ICAM-1 for $\alpha_M\beta_2$, respectively (Rothlein et al., 1986 J. Immunol. 137, 1270; Staunton et al., 1988 Cell 52, 925; Staunton et al., 1989 Nature 339, 61). The ICAMs are monomeric transmembrane proteins that are members of the immunoglobulin superfamily.

The activation of endothelial cells and neutrophils represents an important component of neutrophil-mediated inflammation. Factors that induce cell activation are termed agonists. Endothelial cell agonists, which include small regulatory proteins such as tumor necrosis factor (TNF$\alpha$) and interleukin-1 (IL-1$\alpha$), are released by cells at the site of injury. Activation of endothelial cells results in increased surface expression of ICAM-1 (Staunton et al., 1988 Cell 52, 925) and ELAM-1 (Bevilacqua et al., 1987 Proc. Natl. Acad. Sci. (U.S.A.) 84, 9238). Raised levels of expression of these adhesive molecules on the surface of activated endothelial cells leads to the observed increased adhesivity of neutrophils for the vascular endothelium near sites of injury.

Activation of the neutrophil results in profound changes to its physiological state, including shape change, ability to phagocytose foreign bodies and release of cytotoxic substances from intracellular granules. Moreover, activation greatly increases the affinity of adhesive contacts between neutrophils and the vascular endothelium, perhaps through a conformational change in the $\alpha_M\beta_2$ integrin complex on the neutrophil surface (Vedder and Harlan, 1988 J. Clin. Invest. 81, 676; Buyon et al., 1988 J. Immunol. 140, 3156). Factors that have been reported to induce neutrophil activation include IL-1$\alpha$, GM-CSF, G-CSF, MIP-1, IL-8 (IL-8= interleukin-8, GM-CSF=granulocyte/monocyte-colony stimulating factor, G-CSF=granulocyte-colony stimulating factor), and TNF$\alpha$, the complement fragment C5a, the microbe-derived peptide formyl-Met-Leu-Phe and the lipid-like molecules leukotriene B4 and platelet activating factor (Fuortes and Nathan, 1992, in *Molecular Basis of Oxidative Damage by Leukocytes* Eds Jesaitis, A. J. and Dratz, E. A. (CRC Press) pp. 81–90). In addition, phorbol esters (e.g., phorbol 12-myristate 13-acetate; PMA) represent a potent class of synthetic lipid-like neutrophil agonists. The non-lipid-like agonists cannot pass through the hydrophobic cell membrane of the neutrophil, but activate neutrophils by binding receptors on their surface. Receptors that are occupied by agonist molecules initiate within the neutrophil a cascade of events that ultimately results in the physiological changes that accompany neutrophil activation. This process is known as signal transduction. The lipid-like agonists likely affect neutrophil activation by passing through the plasma membrane at the cell surface and directly interacting with intracellular components of the signal transduction machinery.

There exist two general classes of compounds that modulate the function of neutrophils, and these compounds have been shown to mitigate inflammation. One group of anti-inflammatory compounds functions as inhibitors of neutrophil activation, and presumably adhesion, by acting on components of the signal transduction machinery. A second class of anti-inflammatory compounds blocks neutrophil infiltration into inflammatory foci by acting as direct inhibitors of the adhesive receptors that mediate contact between neutrophils and the vascular endothelium.

Many of the anti-inflammatory compounds currently used as therapeutics, including prostaglandins, catecholamines, and a group of agents known as non-steroidal anti-inflammatory drugs (NSAIDs), are believed to fall into the first category (Showell and Williams, 1989, in *Immunopharmacology*, eds. Gilman, S. C. and Rogers, T. J. [Telford Press, N.J.] pp 23–63). For example, the enhanced adhesiveness observed for TNFα-activated neutrophils has been associated with decreased levels of a mediator of signal transduction, cyclic AMP (cAMP; Nathan and Sanchez, 1990 JCB 111, 2171). Exposure of neutrophils to prostaglandins and catecholamines has been correlated with elevated levels of intracellular cyclic AMP (cAMP; Showell and Williams, 1989). While the signal transduction inhibitors have been used extensively as anti-inflammatory therapeutic agents, they have several disadvantages including poor efficacy in acute inflammatory conditions, lack of specificity and undesirable side-effects such as gastric or intestinal ulceration, disturbances in platelet and central nervous system function and changes in renal function (Insel, 1990 in *The Pharmacological Basis of Therapeutics*, eds. Gilman, A. G., Rall, T. W., Nies, A. S., and Taylor, P. [Pergamon, N.Y.], 8th Ed., pp. 638–681).

Glucocorticoids have long been recognized for their anti-inflammatory properties. Steroid induced inhibition of neutrophils has been reported for several neutrophil functions, including adherence (Clark et al., 1979 Blood 53, 633–641; MacGregor, 1977 Ann. Intern. Med. 86, 35–39). The mechanisms by which glucocorticoids modulate neutrophil function are not well understood, but they are generally believed to involve the amplification or suppression of new proteins in treated neutrophils that play a key role in the inflammatory process (Knudsen et al., 1987 J. Immunol. 139, 4129). In particular, a group of proteins known as lipocortins, whose expression is induced in neutrophils by glucocorticoids, has been associated with anti-inflammatory properties (Flower, 1989 Br. J. Pharmacol. 94, 987–1015). Lipocortins may exert anti-neutrophil effects by interacting with sites on the neutrophil surface (Camussi et al., 1990 J. Exp. Med. 171, 913–927), but there is no evidence to suggest that the lipocortins act by directly blocking adhesive proteins on the neutrophil. Apart from their beneficial anti-inflammatory properties, glucocorticoids have been associated with significant side-effects. These include suppression of pituitary-adrenal function, fluid and electrolyte disturbances, hypertension, hyperglycemia, glycosuria, susceptibility to infection, ulcers, osteoporosis, myopathy, arrest of growth and behavioral disturbances (Insel, 1990).

A second class of anti-inflammatory compounds which are reported as direct inhibitors of neutrophil adhesion to the vascular endothelium has been described recently. Monoclonal antibodies that recognize and block ligand-binding functions of some of these adhesive molecules have proved to be effective in vivo inhibitors of neutrophil-mediated inflammation. In particular, monoclonal antibodies to the β subunit of the β$_2$ integrin complexes on the surface of neutrophils have been shown to prevent a variety of neutrophil-mediated tissue injury in animal models, including pulmonary edema induced by reperfusion (Horgan et al, 1990 Am. J. Physiol. 259, L315–L319), organ injury induced by hemorrhagic shock (Mileski et al, 1990 Surgery 108, 206–212), myocardial damage following ischemia/ reperfusion (Winquist et al, 1990 Circulation III-701), edema and tissue damage following ischemia/reperfusion of the ear (Vedder et al, 1990 Proc. Natl. Acad. Sci. (U.S.A.) 87, 2643–2646), brain edema and death produced by bacterial menningitis (Tuomanen et al, 1989 J. Exp. Med. 170, 959–968), vascular injury and death in endotoxic shock (Thomas et al, 1991 FASEB J. 5, A509) and indomethacin-induced gastric injury (Wallace et al, 1991 Gastroenterology 100, 878–883). Antibodies to other adhesive molecules have also been shown to have anti-inflammatory properties. Monoclonal antibodies that recognize ICAM-1 have been shown to prolong cardiac allograft survival (Flavin et al, 1991 Transplant. Proc. 23, 533–534) and prevent chemically induced lung inflammation (Barton et al, 1989 J. Immunol. 143, 1278–1282). Furthermore, anti-selectin monoclonal antibodies have also proven to be efficacious in animal models of neutrophil-mediated inflammation. Monoclonal antibodies to L-selectin prevent neutrophil emigration into inflamed skin (Lewinshon et al., 1987 J. Immunol. 138, 4313) and inflamed ascites (Jutila et al., 1989 J. Immunol. 143, 3318; Watson et al., 1991 Nature 349, 164). Reports have also described inhibition of neutrophil influx into inflamed lung tissue by anti E-selectin monoclonal antibodies (Mulligan et al., 1991 J. Clin. Invest. 88, 1396; Gundel et al., 1991 J. Clin. Invest. 88, 1407). While monoclonal antibodies to adhesive proteins have demonstrated the feasibility of using neutrophil adhesion inhibitors as anti-inflammatory agents, their utility as therapeutics needs further evaluation.

Soluble adhesive receptors obtained by genetic engineering have been advanced as a further alternative approach as anti-inflammatory compounds. Soluble receptors, in which the transmembrane and intracellular domains have been deleted by recombinant DNA technology, have been used to inhibit neutrophil adhesion to endothelial cells. The functional use of recombinant soluble adhesive molecules has been reported using Mac-1 (Dana et al., 1991 Proc. Natl. Acad. Sci. (U.S.A.) 88, 3106–3110) and L-selectin (Watson et al., 1991).

Recently, a new class of anti-leukocyte compounds collectively termed leumedins has been reported. These compounds have been reported to block the recruitment in vivo of T lymphocytes and neutrophils into inflammatory lesions. The mechanism of action of the leumedins is unclear, but there is evidence that they do not function by blocking neutrophil activation (Burch et al., 1991 Proc. Natl. Acad. Sci. (U.S.A.) 88, 355). It remains to be determined if leumedins block neutrophil infiltration by direct interference with adhesive molecules.

There remains a need for potent, highly specific inhibitors of neutrophil function, in particular, adhesion to vascular endothelium, as a treatment for abnormal neutrophil-mediated inflammation. There are numerous instances whereby compounds from natural sources have been exploited as effective therapeutics; in many cases organisms have evolved such compounds to fill a need for a highly specific effector of the physiology of another organism. Parasites represent a class of organisms whose survival requires that they must evade detection by the host immune system. In this regard, evidence exists for parasite-induced immunosuppression in rodent models (Soulsby, 1987 Immunol Lett. 16, 315–320). It has been reported that saliva of the tick *Ixodes dammini* inhibits neutrophil function (Ribeiro et al, 1990 Exp. Parasitol. 70, 382). An inhibitor of neutrophil function derived from a natural source, such as a parasite, could be a useful anti-inflammatory compound.

The present invention describes a novel inhibitor of neutrophil activity, in particular the adhesion of neutrophils to vascular endothelial cells, derived from the hookworm (*Ancylostoma caninum*) and related species.

SUMMARY OF THE INVENTION

The present invention is directed to a neutrophil inhibitory factor ("Neutrophil Inhibitory Factor"or "NIF") and to enriched compositions comprising Neutrophil Inhibitory Factor. Neutrophil Inhibitory Factor is a protein which is neither an antibody, a member of the integrin or selectin families nor a member of the immunoglobulin super family of adhesive proteins. In a preferred aspect the Neutrophil Inhibitory Factor comprises a protein present in and isolated from or substantially similar to a compound present in a parasitic worm, preferably the hookworm (*Ancylostoma caninum*), that inhibits neutrophil activity, particularly neutrophil adhesion to vascular endothelial cells. This protein appears to act, at least in part, by inhibiting the process of neutrophil activation.

Among other factors, the present invention is based on our finding that the Neutrophil Inhibitory Factor of the present invention represents a pioneering step toward the development of a new generation of anti-inflammatory therapeutic products. This discovery will enable the first therapy for inflammatory disease based entirely on specific inhibition of the inflammatory response. The therapeutic advantages of this novel approach are realized through the specificity of Neutrophil Inhibitory Factor compared to current clinical treatment modalities such as steroids, catecholamines, prostaglandins, and nonsteroidal anti-inflammatory agents. The currently used class of therapeutic agents demonstrates poor efficacy and multiple adverse reactions due to generalized systemic effects that non-specifically target numerous biological processes in addition to the inflammatory process. Nonetheless, the existence of this extensive panel of anti-inflammatory agents, although suboptimal, and the total funds expended by the pharmaceutical industry in research in this area point to significant medical needs and suggest that the discovery of this novel and highly specific Neutrophil Inhibitory Factor will have important applications.

The inflammatory response results in clinical syndromes ranging from debilitating arthritis and asthma to life threatening shock. In view of the severity of these disorders, the vast number of afflicted individuals and the lack of suitable therapeutic intervention, the need for a breakthrough therapy represents a long felt need which has not been met. The Neutrophil Inhibitory Factor of the present invention represents such a breakthrough and provides the potential for a lifesaving therapy which is currently being sought throughout the international medical and pharmaceutical research communities.

The Neutrophil Inhibitory Factor can be isolated by preparing a soluble extract of the worm and fractionating it by chromatography on immobilized Concanavalin A, a molecular sieving matrix, and ceramic hydroxylapatite, and optionally, C4 reverse phase silica. Thus, according to another aspect, the present invention is directed to methods of isolating enriched compositions comprising Neutrophil Inhibitory Factor and the enriched compositions isolated by those methods. The factor can also be partially purified by preparative isoelectric focusing and chromatography on anion exchange media.

In one aspect, the present invention is directed to a composition enriched for Neutrophil Inhibitory Factor comprising a glycoprotein wherein the factor is isolated from a parasitic worm.

An another aspect, the present invention provides a composition enriched for Neutrophil Inhibitory Factor. In one preferred embodiment, the composition is isolated from a parasitic worm. Preferably the composition is enriched at least 200-fold for neutrophil inhibitory activity. Preferably the enriched composition is at least about 90% pure, more preferably, it is chromatographically pure.

The glycoprotein or Neutrophil Inhibitory Factor is preferably acidic as determined by isoelectric focusing, having an isoelectric point of about 4.5, and preferably has a molecular weight in the range of about 38,000 to about 44,000 daltons as determined by laser-desorption time-of-flight mass-spectroscopy.

Preferably, the parasitic worm is a species selected from the phyla Platyhelminthes, Nematoda, Nematomorpha and Acanthocephala, more preferably Nematoda, and especially is isolated from a hookworm species such as those of the super family Ancylostomatidae.

The neutrophil inhibitory activity of the Neutrophil Inhibitory Factor of the present invention may be conveniently demonstrated by its inhibition of at least one biological response in mammalian cells induced by activated neutrophils in an in vitro assay. Suitable assays include those which determine adhesion of neutrophils to vascular endothelial cells or to plastic surfaces, release of hydrogen peroxide by neutrophils or homotypic neutrophil aggregation. Suitable Neutrophil Inhibitory Factors exhibit an $IC_{50}$ of about 500 nM or less, more preferably less than 100 nM.

According to a further aspect of the present invention, methods of preparing biologically active Neutrophil Inhibitory Factor are provided. These methods comprise culturing host cells containing an expression vector which encodes a gene for a glycoprotein having neutrophil inhibitory activity isolated from a hookworm, preferably *Ancylostoma caninum*, which has apparent molecular weight of about 38,000 to about 44,000 daltons as determined by laser-desorption time-of-flight mass spectrometry, and to the Neutrophil Inhibitory Factor produced according to those methods.

Also encompassed within the scope of the invention are isolated nucleic acid molecules, preferably DNA, which code for Neutrophil Inhibitory Factor, vectors, (including cloning and expression vectors) which contain the nucleic acid molecule and host cells transformed with such vectors.

The present invention also provides methods of preparing recombinant Neutrophil Inhibitory Factor using a nucleic acid molecule encoding the Neutrophil Inhibitory Factor. The nucleic acid molecule is expressed in a cultured host cell transformed with a vector containing the nucleic acid molecule operably linked to control sequences recognized by the host cell.

In a further aspect, the present invention is directed to antibodies against Neutrophil Inhibitory Factor, including monoclonal antibodies and hybridomas which produce the monoclonal antibodies, and to immunoassays using the antibodies.

The invention is also directed to pharmaceutical compositions comprising a therapeutically effective amount of Neutrophil Inhibitory Factor and a pharmaceutically acceptable carrier, and the methods of using these pharmaceutical compositions to treat inflammatory conditions, especially to prevent or decrease inflammatory responses. In particular, such pharmaceutical compositions may comprise Neutrophil Inhibitory Factor and a pharmaceutically acceptable carrier, wherein the Neutrophil Inhibitory Factor interacts with neutrophils to inhibit their activity and prevents and/or decreases inflammatory responses in a mammalian host caused by neutrophils when a therapeutically effective amount of Neutrophil Inhibitory Factor is administered.

Other features and advantages of the invention will be apparent from the following descriptions of the preferred embodiments and from the claims.

DETAILED DESCRIPTION OF THE PREFERRED EMBODIMENTS

Neutrophil Inhibitory Factor

Figure 1:
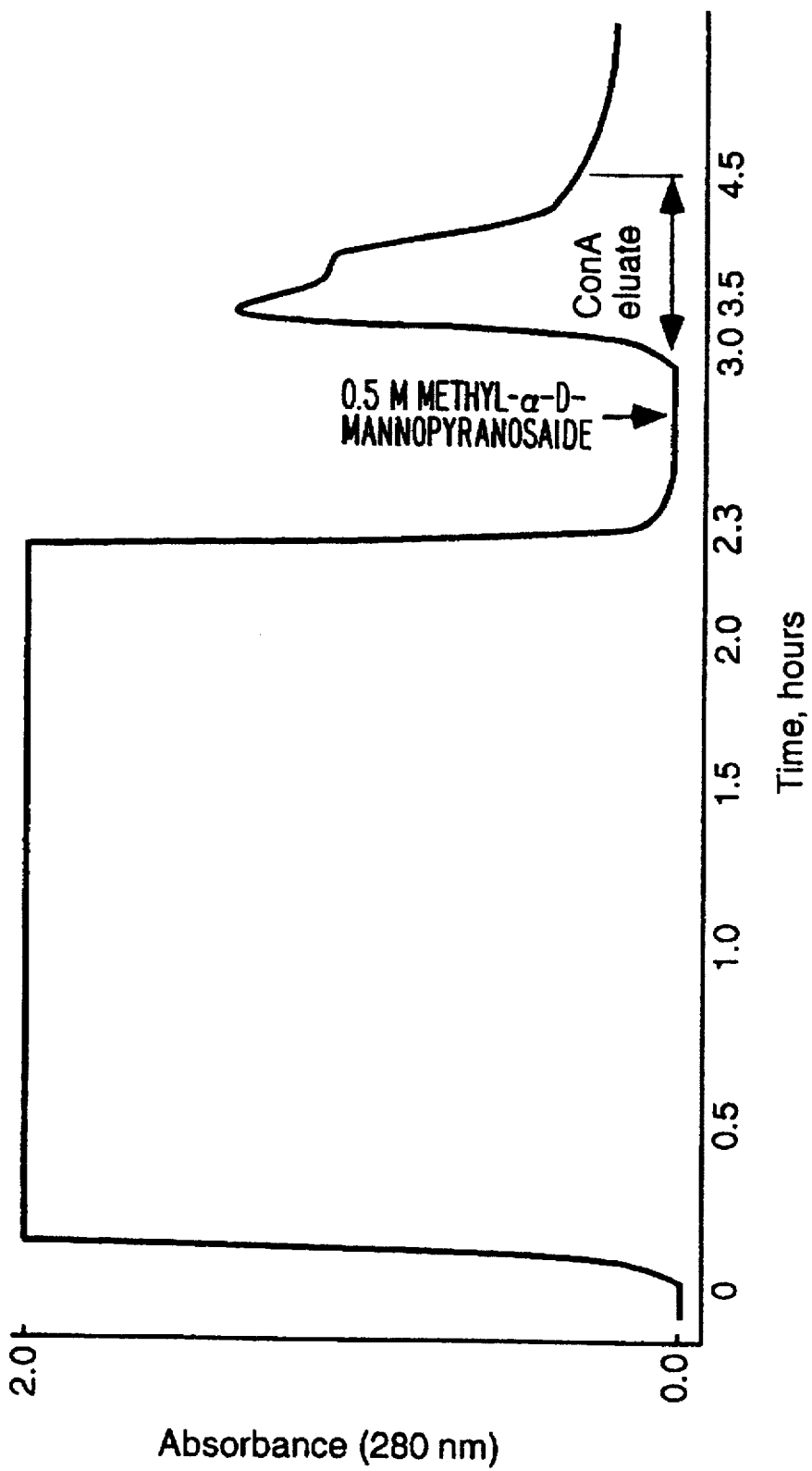
FIG. 1 depicts a chromatogram of Ancylostoma lysate obtained as described in the Example 1(A) run on the Example 1(B) Concanavalin A Sepharose column.

In one aspect, the present invention is directed to compositions which are enriched for Neutrophil Inhibitory Factor, a protein that inhibits neutrophil activity and which is not an antibody, an integrin, a selectin or a member of the immunoglobulin superfamily of adhesive proteins. This neutrophil inhibitory activity includes inhibition of one or more of the following activities by neutrophils: release of hydrogen peroxide, release of superoxide anion, release of myeloperoxidase, release of elastase, homotypic neutrophil aggregation, adhesion to plastic surfaces, adhesion to vascular endothelial cells, chemotaxis, transmigration across a monolayer of endothelial cells and phagocytosis.

According to a preferred embodiment, the Neutrophil Inhibitory Factor comprises a glycoprotein derived from or isolated from a parasitic worm, preferably a nematode, and more preferably an Ancylostoma species, or a compound, preferably a protein, which is substantially similar to said glycoprotein. By substantially similar is meant that the compound exhibits selective neutrophil inhibitory activity similar to that of the glycoprotein, and, preferably has an $IC_{50}$ of about 500 nM or less, more preferably less than 100 nM, as measured by neutrophil activity assays such as those described herein and does not substantially inhibit platelet aggregation at the neutrophil inhibitory concentrations.

These enriched compositions are enriched for Neutrophil Inhibitory Factor using techniques which include chromatography on Concanavalin A Sepharose, hydroxyapatite or an anion exchange column, gel filtration chromatography preferably using Superdex 200, C4 reverse phase HPLC, isoelectric focusing or a combination of those methods or equivalent methods used for separating proteins or proteinaceous factors. For example, in place of Concanavalin A, other immobilized lectins may be used. In place of Superdex 200, other acrylamide- or agarose-based gel filtration media which fractionate proteins in the appropriate molecular weight range may be used; these include those sold under the tradenames Sephacryl and Superose (Pharmacia). Examples of methods of preparing the enriched compositions of the present invention are described in Examples 1 to 4.

In another aspect of the present invention, methods of preparing enriched compositions comprising Neutrophil Inhibitory Factor are provided. Preferably these enriched compositions are at least about 50% pure, that is, they contain at least about 50% Neutrophil Inhibitory Factor. Preferably, the composition is enriched at least about 200-fold. According to another preferred embodiment, substantially pure Neutrophil Inhibitory Factor is prepared. By "substantially pure" is meant at least about 90 percent pure. More preferably the Neutrophil Inhibitory Factor so prepared is chromatographically pure. According to a preferred aspect, methods of preparing substantially pure Neutrophil Inhibitory Factor are provided which comprise subjecting a lysate from a parasitic worm to the following isolation steps (a) chromatography on Concavalin-A Sepharose, and (b) gel filtration on Superdex 200, and (c) chromatography on ceramic hydroxyapatite. The Neutrophil Inhibitory Factor may be then subjected to the further isolation step of reverse phase high performance liquid chromatography (HPLC) using a C4 column.

The Neutrophil Inhibitory Factor of the present invention preferably comprises a purified glycoprotein. This may be determined by evaluating binding to Concanavalin A Sepharose (see Example 1(B)) and by positive testing as a glycoprotein in GlycoTrack™ diagnostic assay for the presence of carbohydrate groups (see Example 6). This glycoprotein is acidic and exhibits an isoelectric point of about 4.5 as determined by isoelectric focusing (see Example 2). It has an observed molecular weight of about 41,000 daltons (± 3,000) as determined by laser-desorption time-of-flight mass spectrometry (see Example 5). Its behavior when subjected to SDS-polyacrylamide gel electrophoresis indicated that it contained multiple disulfide bonds, since the reduced glycoprotein migrated on the gel at a significantly higher apparent molecular weight (see Example 4). The glycoprotein was demonstrated to specifically inhibit neutrophil activity and not to act as a general cytotoxin in another cell adhesion assay. This glycoprotein was demonstrated to inhibit neutrophil adhesion to vascular endothelial cells and homotypic neutrophil aggregation; one such enriched composition (see Example 1(D)) exhibited an $IC_{50}$ of about 10 nM. An $IC_{50}$ is that concentration of inhibitor giving 50% inhibition of the measured activity (see Example A). This enriched composition was demonstrated to inhibit hydrogen peroxide release from neutrophils and neutrophil adhesion/ spreading on plastic. The Example 1(D) preparation had an $IC_{50}$ of about 10 nM. An enriched composition of the neutrophil inhibitory factor was shown to have no inhibitory effect on platelet aggregation (see Example B).

According to a preferred aspect, the Neutrophil Inhibitory Factor comprises a glycoprotein which is isolated from a parasitic worm, preferably a nematode. Suitable parasitic worms include those selected from species of the phyla Platyhelminthes, Nematoda, Nematomorpha and Acanthocephala. An especially preferred source is the endoparasitic hookworm species *Ancylostoma caninum*. Substantially similar compounds may be isolated from other nematode species, as well as from other endoparasites of other phyla. Preferred sources include other parasites, including other parasitic worms, other endoparasitic nemotodes and especially other hookworm species, including *Ancylostoma braziliense, Ancylostoma ceylanicum, Ancylostoma duodenale, Ancylostoma japonica, Ancylostoma malayanum, Ancylostoma tubaeforme, Bunostomum phlebotomum, Cyclodontostomum purvisi, Necator americanus, Necator argentinus, Necator suillus,* and *Uncinaria stenocephala.*

Isolation of DNA Sequences That Encode Neutrophil Inhibitory Factor

As described above, one example of Neutrophil Inhibitory Factor (NIF) of this invention which comprises a glycoprotein has been isolated in substantially pure form. Using standard procedure, those of ordinary skill in the art can use this protein to derive its amino acid sequence. For example, the protein may be analyzed to determine an N-terminal sequence, or fragments of the protein can be produced by enzymatic or other specific digestion procedures and the sequence of the terminal amino acids of those fragments determined. Such amino acid sequences, even if only between five and six contiguous amino acids in length, will provide sufficient information to determine potential DNA sequences of a gene encoding this protein. If two or three such amino acid fragments are sequenced a plurality of appropriate oligonucleotides can be synthesized using standard procedure, and can be used to probe a genomic or cDNA library of hookworm (or other source) DNA to isolate the gene or fragments thereof encoding the sequenced protein. Those in the art will recognize that these oligonucleotides can be designed using standard parameters such that the oligonucleotide is chosen to encode the chosen acid sequence. For example, it is common to use a mixture of oligonucleotides as a probe for any particular sequence of amino acid, with each oligonucleotide having the same nucleotide base sequence except at specific bases which are varied to take into account the various redundant codons that might code for any particular amino acid. It is of course desirable to choose an amino acid sequence which is encoded by as few oligonucleotides as possible. In addition, the various redundant codons may be specifically selected to represent those codons that are most preferred in, for example, hookworm nucleic acid.

In addition, the above-described isolated pure protein can be used to form antibodies by standard procedures. Such antibodies may include monoclonal or polyclonal antibodies and can be used to screen bacteriophage λgt11 expression libraries containing other source (e.g., hookworm) DNA. In this manner, any particular clone which includes nucleic acid encoding the Neutrophil Inhibitory Factor can be readily identified using standard procedures.

Genomic DNA libraries of a hookworm, for example, can be formed using standard procedure to isolate the genomic DNA of the hookworm, fractionating that DNA using either a random procedure, such as sonication, or a specific procedure such as restriction endonuclease digestion and ligation of those fragments into an appropriate vector, such as a bacteriophage lambda (λ), plasmid or cosmid vector. Such a library can be screened for useful clones by nucleic acid hybridization using the oligonucleotide mixtures described above. More preferably, however, a cDNA library can be constructed by isolation of total hookworm RNA, passage of that RNA over an oligo-dT column to purify the poly(A)-containing RNA (i.e., messenger RNA), and reverse transcription of such RNA to produce DNA fragments representative of the RNA (i.e., cDNA). These cDNA fragments can be inserted using standard procedures into any desired vector, for example, an expression vector such as a commercially available *E. coli* expression vector such as bacteriophage λgt11 (for expression in *E. coli*), or into a plasmid pcDNA-1 which can be expressed in mammalian COS7 cells.

The biological activity of the protein expressed in each clone of the plasmid expression library can be readily assayed using the neutrophil inhibitory activity assays described herein or other suitable assays. Alternatively, the antibodies described above can be used to probe for immunoreactive protein expressed from clones in the bacteriophage expression libraries (e.g., λgt11). It is particularly preferred to screen various libraries in sub-pools, for example, of 999 clones at a time to determine which of those sub-pools includes a positive clone. When a positive clone is isolated a grid of the 999 colonies can be formed on a 33×33 plate and each of the 33 clones in each row and column in the plate assayed simultaneously (i.e., in 66 preparations) to identify the desired clone.

Once the desired clone is isolated, its structure is analyzed by standard procedures, for example, by DNA sequencing to determine whether it encodes the whole of the desired protein. If it does not, that clone can be used to screen further cDNA or genomic libraries for other full-length clones, or the DNA can be used to hybrid select RNA present in the hookworm, or other source, and more selective cDNA libraries formed from that RNA using procedures described above.

Applicants note that by using techniques such as those described above, as well as similar and equivalent techniques, DNA sequences which encode Neutrophil Inhibitory Factor from other source animals may be isolated and used to express recombinant Neutrophil Inhibitory Factor.

Should immunoreactive material be expressed from an expression library, the expression vectors described above, or derivatives thereof, can be used for expression of recombinant protein with biological activity equivalent to that of the native protein. Such recombinant protein is useful in this invention.

Expression of Recombinant Neutrophil Inhibitory Factor

The cDNA encoding Neutrophil Inhibitory Factor may be inserted into a replicable vector for expression, resulting in the synthesis of biologically active recombinant Neutrophil Inhibitory Factor. Many vectors are available for expression of heterologous proteins and selection of the appropriate vector will depend primarily on the desired properties of the host cell. Each of the available vectors contain various components specific to the host cell to be transformed. The vector components or control elements generally include, but are not limited to, one or more of the following: a signal sequence, an origin of replication, one or more marker genes, a promoter, an enhancer element and a transcription termination sequence. Once the expression vector containing the inhibitor is constructed, a suitable host cell is transfected or transformed with the expression vector, and recombinant Neutrophil Inhibitory Factor is purified either from the host cell itself or the host cell growth medium.

In general, the signal sequence may be a component of the vector, or it may be encoded by the Neutrophil Inhibitory Factor DNA that is inserted into the vector. If the native inhibitory factor is a secreted gene product (i.e., from the hookworm (or other source) cells), then the native pro-Neutrophil Inhibitory Factor from hookworm DNA may encode a signal sequence at the amino terminus of the polypeptide that is cleaved during post-translational processing of the polypeptide to form the mature Neutrophil Inhibitory Factor.

All vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacterial, yeast, insect and mammalian cells. The origin of replication from the plasmid pBR322 is suitable for most for most Gram-negative bacteria, the 2μ plasmid origin is suitable for yeast, the baculovirus origin is suitable for some insect cells (e.g., Sf9 cells; CRL1711) and various viral origins (e.g., SV40, adenovirus) are useful for cloning vectors in mammalian cells.

Expression vectors should contain a selection gene, also termed a selectable marker. This gene encodes a protein necessary for the survival or growth of transformed host cells grown in selective culture medium. Host cells not transformed with the vector containing the selection gene will not survive in the culture medium. Typical selection genes encode proteins that (a) confer resistance to antibiotics or other toxins, e.g., ampicillin, neomycin or methotrexate, (b) complement auxotrophic deficiencies, or (c) supply critical nutrients not available from complex media.

Expression vectors contain promoters that are recognized by the host organism. Promoters are untranslated sequences located upstream (5') to the start codon of a structural gene (generally within about 100 to 1000 base pairs) that control the transcription and translation of a particular nucleic acid sequence, such as hookworm Neutrophil Inhibitory Factor, to which they are operably linked. A large number of promoters recognized by a variety of potential host cells are well known. These promoters are operably linked to DNA encoding the Neutrophil Inhibitory Factor by inserting the latter into the vector in a way such that the 5' terminus of the Neutrophil Inhibitory Factor DNA is in close linear proximity to the promoter.

Transcription of a DNA encoding the Neutrophil Inhibitory Factor of this invention by higher eukaryotes is often increased by inserting an enhancer sequence into the vector (for example see Kriegler, 1991). Enhancers are cis-acting elements of DNA, usually about 10–300 base pairs in length, that act on a promoter to increase its transcription. Enhancers are relatively orientation and position independent. Typically, one will use an enhancer from a eukaryotic cell virus for expression in mammalian cells. Examples include the SV40 enhancer, the cytomegalovirus early promoter enhancer and the adenovirus enhancers.

Expression vectors used in eukaryotic (i.e., non-bacterial) host cells will also contain sequences necessary for the termination of transcription and for stabilizing the mRNA. Such sequences are commonly available from the 5' end and, occasionally from the 3' untranslated regions of eukaryotic or viral DNAs.

Suitable host cells for the expression vectors described herein include bacterial, yeast, insect or mammalian cells. Preferred bacteria are *E. coli* strains, preferred yeast are *Saccharomyces cerevisiae* and *Pichia pastoris*, a preferred insect cell line is Sf9 (ATCC# CRL 1711) and preferred mammalian cell lines are COS-7 (ATCC# CRL 1651), CHO-K1 (ATCC# CCL 61) and HeLa (ATCC# CCL 2). These examples of host cells are illustrative rather than limiting. Preferably the host cell should secrete minimal amounts of proteolytic enzymes. Particularly suitable host cells for the expression of glycosylated Neutrophil Inhibitory Factor are derived from multicellular organisms. Such host cells are capable of complex post-translational processing and glycosylation activities of expressed proteins.

Host cells are transfected and preferably transformed with the above-described expression vectors of this invention and cultured in conventional nutrient media modified as appropriate for inducing promoters and selecting transformants. Transfection refers to the taking up of an expression vector by a host cell. Numerous methods of transfection are known to the ordinarily skilled artisan, for example, calcium phosphate coprecipitation, spheroplasting transformation and electroporation. Successful transfection is generally recognized when any indication of the operation of this vector occurs within the host cell. Transformation means introducing DNA into an organism so that the DNA is replicable, either as an extrachromosomal element or chromosomal integration. Depending on the host cell used, transformation is done using standard techniques appropriate to such cells (e.g., calcium chloride or electroporation for bacterial cells; spheroplasting or electroporation for yeast cells; calcium phosphate or electroporation for insect and mammalian cells).

The recombinant hookworm neutrophil inhibitor preferably is recovered from the culture medium as secreted polypeptide, although it may also be recovered from host cell lysates when directly expressed without a signal or secretory sequence. The expressed hookworm neutrophil inhibitor may be purified from culture medium or from cell lysates by a variety of separation techniques including, but not limited to, gel filtration, affinity and ion exchange chromatography, hydroxyapatite chromatography, C4 reverse-phase HPLC and preparative isoelectric chromatography.

Amino Acid Sequence Variants of the Neutrophil Inhibitory Factor

Amino acid sequence variants of the Neutrophil Inhibitory Factor are prepared by introducing nucleotide changes into the Neutrophil Inhibitory Factor DNA, isolated as described above. Such variants include substitutions of residues within the amino acid sequence of the Neutrophil Inhibitory Factor. Any combination of substitutions can be made to arrive at the final construct, provided that the final construct possesses certain desired characteristics. The desired characteristic includes, but is not limited to, an increased potency over the wild-type Neutrophil Inhibitory Factor. One possible method for preparing variants of the Neutrophil Inhibitory Factor is mutagenesis with base-specific chemical mutagens as described in detail by Pine and Huang (1987, Methods Enzymol. 154, 415–430). Once variant inhibitor DNAs have been constructed, variant recombinant forms of Neutrophil Inhibitory Factor may be synthesized utilizing expression systems as described above.

Preparation of Fragments of Neutrophil Inhibitory Factor

Another aspect of the present invention is directed to peptide fragments having neutrophil inhibitory activity which are prepared by proteolytic or chemical methods starting with the chromatographically pure Neutrophil Inhibitory Factor of the present invention.

Active peptide fragments, with or without sugar moieties, may be generated by using enzymatic or chemical techniques. Proteolytic cleavage can be accomplished by digestion of the inhibitor with one or more of the following enzymes: chymotrypsin, trypsin, leucine aminopeptidase, endoproteinase Glu-C, endoproteinase Lys-C, endoproteinase Arg-C, or endoproteinase Asp-N (Carrey, E. A., 1989 *Protein Structure, A Practical Approach*, pp. 117–143, T. E. Creighton, ed. IRL Press, New York). Chemical digestion of the inhibitor may be accomplished by cyanogen bromide, hydroxylamine, or 2-nitro-5-thiocyanobenzoate cleavage (Carrey, E. A., 1989, ibid.). Sugar moieties can be removed from either the peptide fragments or intact neutrophil inhibitory protein enzymatically with one or more of the following enzymes: glycopeptidase F, endoglycosidase H, endoglycosidase F, or endoglycosidase D as described by Keesey (Keesey, J., 1987 *Biochemica Information*, pp. 147–165, J. Keesey, ed., Boehringer Mannheim Biochemicals, Indianapolis). Alternatively, glycosylation of the intact inhibitor may be suppressed by expression of the protein in bacterial cells or by the inclusion of inhibitors of glycosylation in the eukaryotic cell culture growth medium. Inhibitors of glycosylation and their uses are described in the art (e.g., Keesey, J. 1987 *Biochemica Information*, pp. 135-141, J. Keesey, ed., Boehringer Mannheim Biochemicals, Indianapolis). Separation of active fragments from inactive fragments may be accomplished by conventional, low, medium, or high pressure chromatographic techniques known in the art.

Utility and Applications

The Neutrophil Inhibitory Factor of the present invention has potent neutrophil inhibitory activity and, thus, may be used as an inhibitor of neutrophil activity, including neutrophil activation, as well as for preventing or treating inflammatory conditions characterized by neutrophil activation.

Thus, the Neutrophil Inhibitory Factor will be useful in the treatment of inflammation in which neutrophils play a significant role. While Applicants do not wish to be bound to any theory or mode of activity, it is believed that this compound will interfere with the inflammatory response which is set into action by neutrophil-endothelial cell interactions. Thus, where adhesion of neutrophils to the endothelium is prevented, the neutrophils will be unable to transmigrate to tissue to elicit a proinflammatory response with consequent tissue damage. Inhibition of neutrophil-neutrophil adhesion and subsequent aggregation by these compounds should also prevent microvascular occlusion. Thus, these compounds will be useful in treating a variety of clinical disorders, including shock, stroke, acute and chronic allograft rejection, vasculitis, sepsis, rheumatoid arthritis, inflammatory skin diseases, inflammatory bowel disease, adult respiratory distress syndrome (ARDS), and ischemia-reperfusion injury following myocardial infarction, in which neutrophil infiltration and activation has been implicated.

The ability of the Neutrophil Inhibitory Factor of the present invention to inhibit neutrophil activity makes it useful in inhibiting the physiological processes of inflammation, ischemia, and other neutrophil mediated tissue damage. The specific activities of the Neutrophil Inhibitory Factor in carrying out these related functions makes it particularly useful as therapeutic and/or diagnostic agents.

Neutrophil inhibitory activity may be demonstrated by various assays, including neutrophil adhesion to endothelial cells or plastic, homotypic neutrophil aggregation and hydrogen peroxide release by neutrophils. See Example A.

Antibodies, both monoclonal and polyclonal, directed to Neutrophil Inhibitory Factor of the present invention are useful for diagnostic purposes and for the identification of concentration levels of the subject peptides in various biological fluids. To prepare the subject antibodies, any one of a number of conventional techniques which are known in the art can be employed. In one such technique, polyclonal antibodies are synthesized by injecting an animal (for example a rabbit) with one or more compounds of the invention. After injection, the animal naturally produces antibodies to these compounds. When the antibody concentration (or titer) reaches a sufficient level, antibody-containing blood, called antiserum, is then drawn from the animal, serum is prepared, and the compound-specific antibody is isolated from other antibodies in the serum by any one of a number of separation techniques (for example, affinity chromatography). Monoclonal antibodies may be prepared using the technique of Kohler and Milstein, Nature 256, 495-497 (1975) and other conventional techniques known to those skilled in the art. (See, e.g., Harlow and Lane, *Antibodies. A Laboratory Manual* (Cold Spring Harbor Laboratory, 1988) the disclosures of which is incorporated herein by reference).

An additional aspect of the present invention is directed to monoclonal antibodies which recognize Neutrophil Inhibitory Factor. Also considered as part of the present invention are hybridomas which synthesize such monoclonal antibodies. These hybridomas are produced by conventional techniques such as those described by Harlow and Lane, Id., the disclosures of which is incorporated herein by reference.

A further aspect of the present invention is directed to immunoassays using the antibodies against Neutrophil Inhibitory Factor. Depending on the particular use, one of various immunoassay formats may be selected. Suitable immunoassays are described by Harlow and Lane, Id. see especially pages 553 to 612, the disclosures of which are incorporated herein by reference. These immunoassays may be used as diagnostics such as to detect infection of a mammalian host by a parasitic worm, by assay for Neutrophil Inhibitory Factor from a parasitic worm in a tissue of the mammalian host. Also such immunoassays may be used in the detection and isolation of Neutrophil Inhibitory Factor from tissue homogenates, cloned cells and the like.

In another aspect of the present invention, the Neutrophil Inhibitory Factor (NIF) can be used in a test method to screen other compounds, such as small molecule peptide analogs, for neutrophil inhibitory activity. According to one embodiment, a binding assay is used to establish binding levels of detectable labelled NIF to neutrophils. Suitable detectable labels to be used for labelling NIF include conventionally used enzyme labels, radioactive isotopes and other labels known to those skilled in the art. According to one suitable assay protocol, labelled NIF and neutrophils are co-incubated in solution for a sufficient time to allow binding. Unbound labelled NIF is removed from bound NIF by methods such as centrifugation, filtration or other suitable methods and bound NIF is determined. According to an alternate protocol, neutrophils are immobilized on a plastic surface by natural adhesion or chemical fixation such as by glutaraldehyde or similar chemicals; the labelled NIF is co-incubated with the immobilized neutrophils and unbound NIF is removed by washing. Bound NIF is determined. Compounds, such as small molecule peptide analogs, are screened for neutrophil inhibitory activity according to the following protocol. Test compounds are preincubated in solution with neutrophils and the preincubated solution brought into contact with labelled NIF. The effect of test compound on NIF-neutrophil binding is then determined. According to an alternative screening procedure, test compounds can be screened for activity in preventing NIF binding to neutrophils employing an assay similar to the neutrophil-plastic adhesion assay of Example A(C). Test compounds are preincubated in solution with neutrophils. Labelled NIF is then added and the resulting solution is incubated. The incubated solution is assayed for effect on plastic binding by activated neutrophils as described in Example A(C). The effect of test compound-NIF incubation solution on plastic binding is determined in comparison with solution incubated with labelled NIF alone.

With suitable adjuvants NIF can be used as a vaccine against parasitic worm infections in mammals. Immunization with NIF vaccine may be used in both the prophylaxis and therapy of parasitic infections. NIF fragments and synthetic polypeptides having the amino acid sequence of NIF may also be used as vaccines. Disease conditions caused by parasitic worms may be treated by administering to an animal infested with these parasites substances which antagonize NIF. Compounds may be screened for their anti-NIF effect according to the screening method described herein above. Example of such antihelminic agents include antibodies to NIF, both naturally occurring antibodies isolated from serum and polyclonal and monoclonal antibodies described hereinabove. Chemically synthesized compounds which act as inhibitors of NIF also are suitable antihelminic agents.

Formulations

The enriched compositions of the present invention may be formulated and used as tablets, capsules or elixirs for oral administration; suppositories for rectal administration; sterile solutions, suspensions for injectable administration; and the like. The dose and method of administration can be tailored to achieve optimal efficacy but will depend on such factors as weight, diet, concurrent medication and other factors which those skilled in the medical arts will recognize. Generally, an amount between 0.01 µg/kg to 100 mg/kg body weight/day is administered dependent upon the potency of the composition used.

The present invention also encompasses pharmaceutical compositions prepared for storage and subsequent administration which comprise a pharmaceutically effective amount of an enriched composition as described herein in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985). Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

In practicing the methods of the invention, the enriched compositions can be used alone or in combination with one another, or in combination with other therapeutic or diagnostic agents. These compositions can be utilized in vivo, ordinarily in a mammal, preferably in a human, or in vitro. In employing them in vivo, the compositions can be administered to the mammal in a variety of ways, including parenterally, intravenously, subcutaneously, intramuscularly, colonically, rectally, nasally or intraperitoneally, employing a variety of dosage forms. As will be readily apparent to one skilled in the art, the useful in vivo dosage to be administered and the particular mode of administration will vary depending upon the mammalian species treated, the particular composition employed, and the specific use for which these compositions are employed. The determination of effective dosage levels, that is the dosage levels necessary to achieve the desired result, will be within the ambit of one skilled in the art. Typically, applications of compositions are commenced at lower dosage levels, with dosage level being increased until the desired effect is achieved.

The dosage for the compositions of the present invention can range broadly depending upon the desired affects and the therapeutic indication. Typically, dosages will be between about 0.01 µg and 100 mg/kg, preferably between about 0.01 and 10 mg/kg, body weight. Administration is preferably parenteral, such as intravenous on a daily or as-needed basis.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

To assist in understanding the present invention, the following examples are included which describe the results of a series of experiments. The following examples relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

EXAMPLE 1

ISOLATION OF NATIVE NEUTROPHIL ACTIVATION INHIBITOR FROM HOOKWORM LYSATE (A) Preparation of Ancylostoma Lysate Frozen canine hookworms (Ancylostoma caninum) were obtained from Antibody Systems (Bedford, Tex.). Hookworms were stored at −70° C. until used for homogenate.

Hookworms were homogenized on ice in homogenization buffer [0.02M Tris-HCl pH 7.4, 0.05M NaCl, 0.001M $MgCl_2$, 0.001M $CaCl_2$, $1.0 \times 10^{-5}$M dithiothreitol, $1.0 \times 10^{-5}$M E-64 Protease Inhibitor (CAS 66701-25-5), $1.0 \times 10^{-6}$M pepstatin A (isovaleryl-Val-Val-4-amino-3-hydroxy-6-methyl-heptanoyl-Ala-4-amino-3-hydroxy-6-methylheptanoic acid, CAS 26305-03-3), $1.0 \times 10^{-5}$M chymostatin (CAS 9076-44-2), $2.0 \times 10^{-5}$M APMSF (amidinophenylmethylsulfonyl fluoride-HCl), 5% (v/v) glycerol] using a Tekmar Tissuemizer homogenizer. The protease inhibitors E64, pepstatin A, chymostatin, and APMSF were obtained from Calbiochem (La Jolla, Calif.). Approximately 3–6 ml of homogenization buffer was used to homogenize each gram of frozen worms (approximately 500 worms). Insoluble material was pelleted by two sequential centrifugation steps: $40,000 \times g_{max}$ at 4° C. for 20 minutes followed by $105,000 \times g_{max}$ at 4° C. for 40 minutes. The supernatant solution was clarified by passage through a 0.2 µm cellulose acetate filter (CoStar).

(B) Concanavalin A Sepharose Chromatography of Ancylostoma Lysate

Hookworm lysate (79 ml) was adsorbed to 16 mL of Concanavalin A Sepharose Concanavalin-A coupled to matrix of 4% agarose (Pharmacia) pre-equilibrated with Con A buffer [0.02M Tris-HCl, pH 7.4, 1M NaCl, 0.001M $CaCl_2$, 0.001M $MnSO_4$, $1 \times 10^{-5}$M dithiotreitol] by recycling it through a 1.6×8 cm column at a flow rate of 3 ml/min (90 cm/hour) for 2 hours. The column was at room temperature (24° C.) while the reservoir of lysate was maintained on ice throughout the procedure. The column was subsequently washed with 80 ml of Con A buffer. The Con A buffer in the column was displaced with buffer containing 0.5M methyl-alpha-mannopyranoside and flow stopped for 30 minutes. Flow was then restarted at a flow rate of 0.5 ml/min (15 cm/hour). Material that had inhibitory activity in neutrophil function assays was eluted with approximately three column volumes of Con A buffer containing 0.5M methyl-alpha-mannopyranoside (CAS 617-04-09). The yield of neutrophil adhesion inhibitory activity in this step was approximately 38%.

FIG. 1 depicts Concanavalin A Sepharose chromatography of the Ancylostoma lysate performed as described above. Absorbance at 280 nm was plotted as a function of time.

(C) Molecular Sieve Chromatography Using Superdex 200

Active fractions eluted from immobilized Concanavalin A (see step (B) above) and concentrated by ultrafiltration at 4° C. using an Amicon stirred cell equipped with a 10,000 Dalton cut-off membrane (YM10), then 5–20 ml of the concentrate were loaded on a 2.6 cm×60 cm column of Superdex 200 prep gel filtration media comprising a matrix of cross-linked agarose and dextran having a separation range of 10 to 600 KD. (Pharmacia) attached in series with an identical column (combined dimensions of 2.6×120 cm). Both columns were pre-equilibrated with 0.01M potassium phosphate, pH 7.35, 0.150M NaCl, 1×10$^{-5}$M dithiotreitol at 24° C. The chromatography was conducted at a flow rate of 1.5 ml/min; anti-adhesion activity typically eluted 395–410 ml into the run ($K_{av}$ of 0.46, see FIG. 2). This elution volume would be expected for a globular protein with a molecular mass of 50,000. The yield of neutrophil function inhibitory activity in this step was typically 70–80%. If the ionic strength of the chromatography buffer employed was decreased to 0.01M sodium phosphate, pH 7.00 and 10% (v/v) glycerol added, the activity eluted substantially earlier ($K_{av}$=0.34) suggesting that under such conditions the protein either aggregates or changes its conformation (assuming a larger Stoke's radius).

Figure 2:
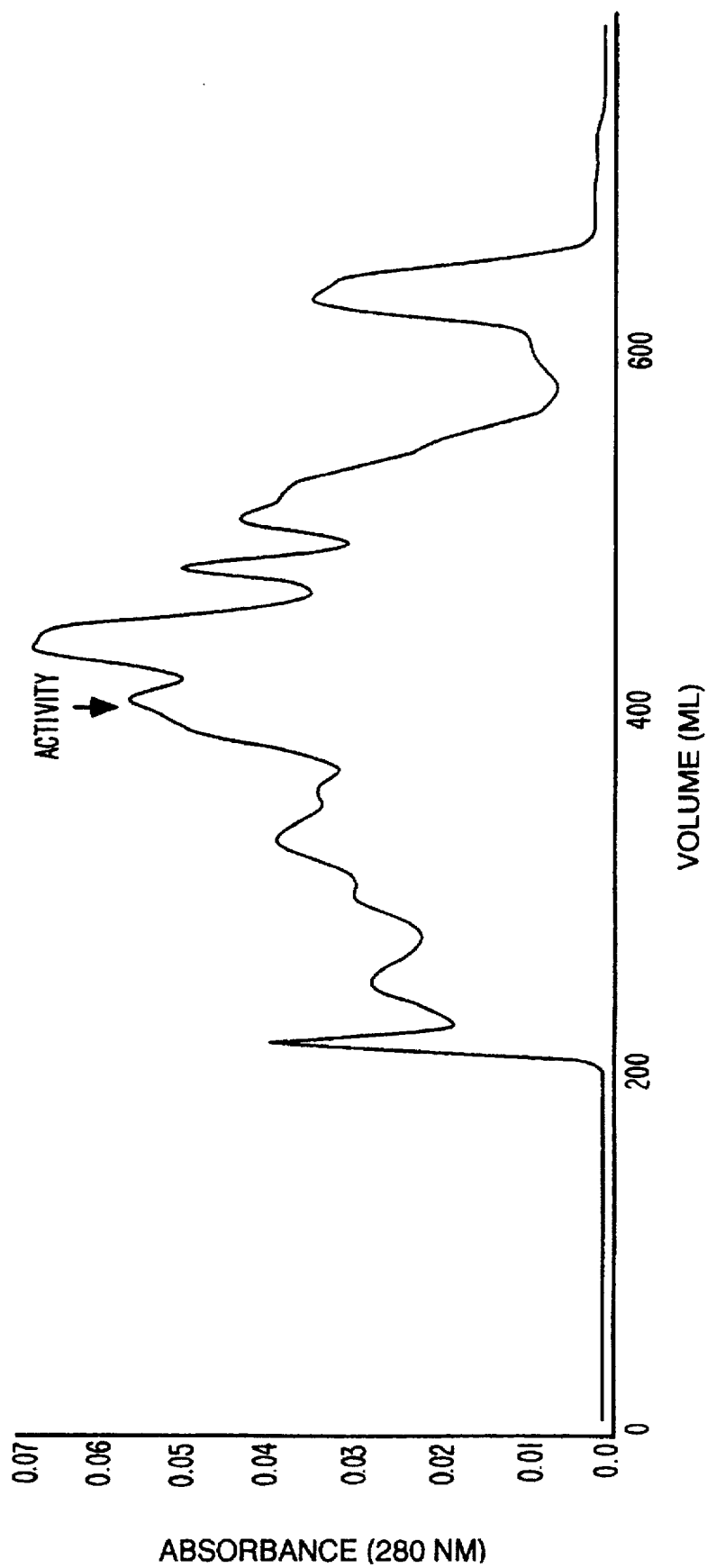
FIG. 2 depicts a chromatogram of Concanavalin A-purified Ancylostoma lysate run on the Example 1(C) Superdex 200 column.

FIG. 2 depicts Superdex 200 Chromatography of Concanavalin A-Purified Ancylostoma Lysate. Absorbance at 280 nm is plotted versus elution volume. Active fractions eluted from immobilized Concanavalin A (see step (B) above) and concentrated by ultrafiltration at 4° C. using an Amicon stirred cell equipped with a 10,000 Dalton cut-off membrane (YM10), then 5–20 ml of the concentrate were loaded on a 2.6 cm×60 cm column of Superdex 200 prep (Pharmacia) attached in series with an identical column (combined dimensions of 2.6×120 cm). Both columns were pre-equilibrated with 0.01M potassium phosphate, pH 7.35, 0.150M NaCl, 1×10$^{-5}$M dithiotreitol at 24° C. The chromatography was conducted at a flow rate of 1.5 ml/min; activity eluted 395–410 ml into the run ($K_{av}$ of 0.46).

(D) Ceramic-Hydroxyapatite Chromatography

Material purified by molecular sieve chromatography was concentrated five-fold by ultrafiltration using an Amicon stirred cell equipped with a 10 kilodalton cut-off membrane at 4° C. and then diluted ten-fold with water. The desalted sample was loaded on a 0.8×10 cm column of ceramic hydroxyapatite ("HA") (Pentax, American International Chemical, Inc., 2 μm) equilibrated with 0.001M potassium phosphate, pH 7.00, 1×10$^{-5}$M CaCl$_2$, 1.0×10$^{-5}$M dithiothreitol at 24° C. The loading was conducted at a flow rate of 0.8 ml/min (95.5 cm/hour). The column was developed with a 50 ml linear gradient of potassium phosphate ranging from 0.001M to 0.0375M at a flow rate of 0.5 ml/minute. Neutrophil inhibitory activity eluted sharply at 0.025M potassium phosphate and then trailed to 0.0325M potassium phosphate (fractions 37 to 48). The yield of activity in this step was approximately 48%.

Figure 3:
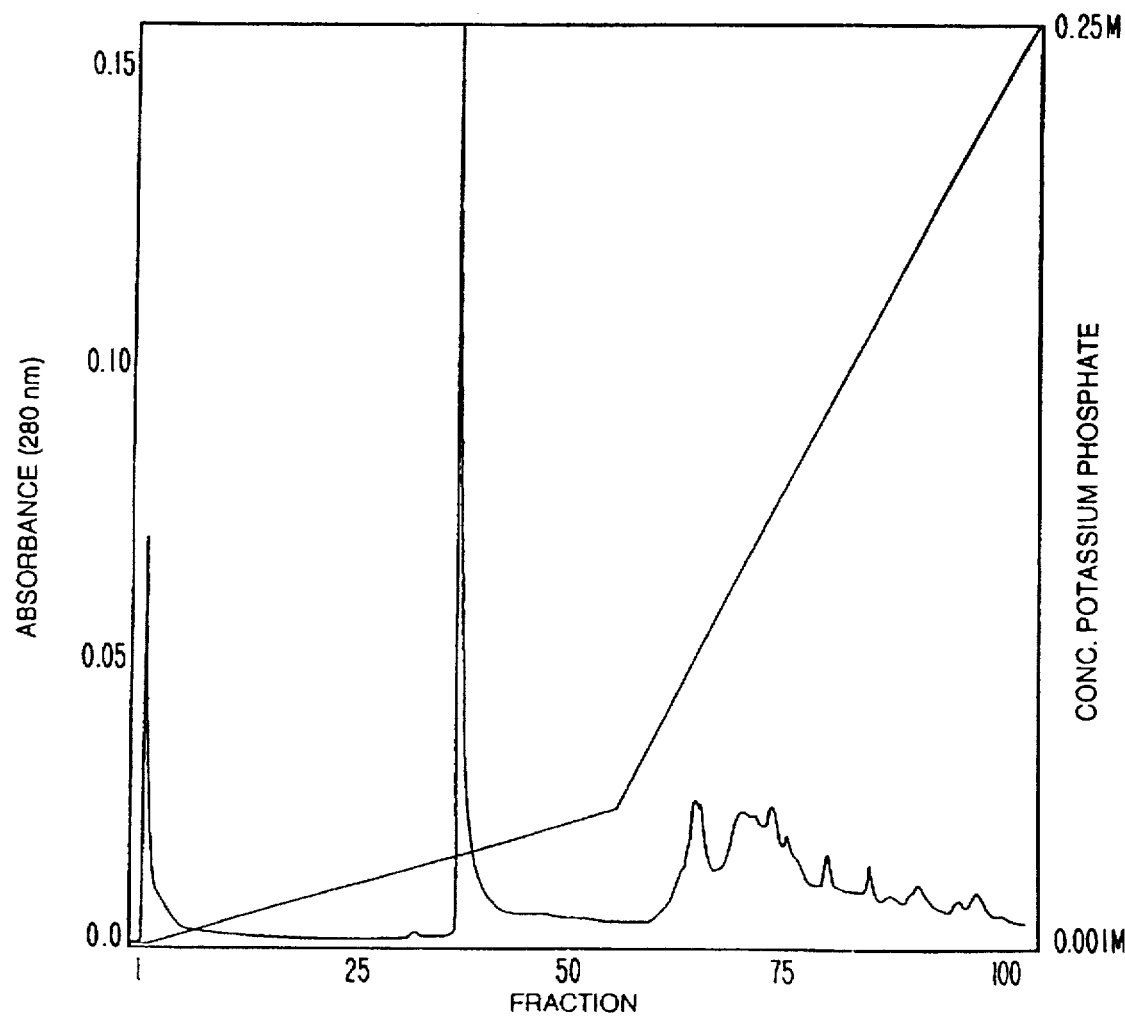
FIG. 3 depicts a chromatogram of the Concanavalin A Sepharose/Superdex purified Ancylostoma lysate run on the Example 1(D) ceramic hydroxyapatite column.

FIG. 3 depicts Ceramic Hydroxylapatite Chromatography of Superdex/Concanavalin A-Purified Ancylostoma lysate plotting absorbance at 280 nm and potassium phosphate concentration versus fraction number. Neutrophil inhibitory activity eluted in fractions 37 to 48.

(E) Reverse Phase HPLC

Hookworm lysate fractionated by chromatography on Concanavalin A Sepharose, Superdex, and ceramic hydroxylapatite (~100 μg) was loaded on to a 0.48×15 cm column of 300 Å C4 (Vydac) which was then developed with a linear gradient of 0–60% acetonitrile in 0.1% trifluoroacetic acid at 1 ml/minute with a rate of 1% change in acetonitrile/minute.

Neutrophil inhibitory activity typically elutes between 41 and 45% acetonitrile, the activity corresponding with a broad peak.

Figure 4:
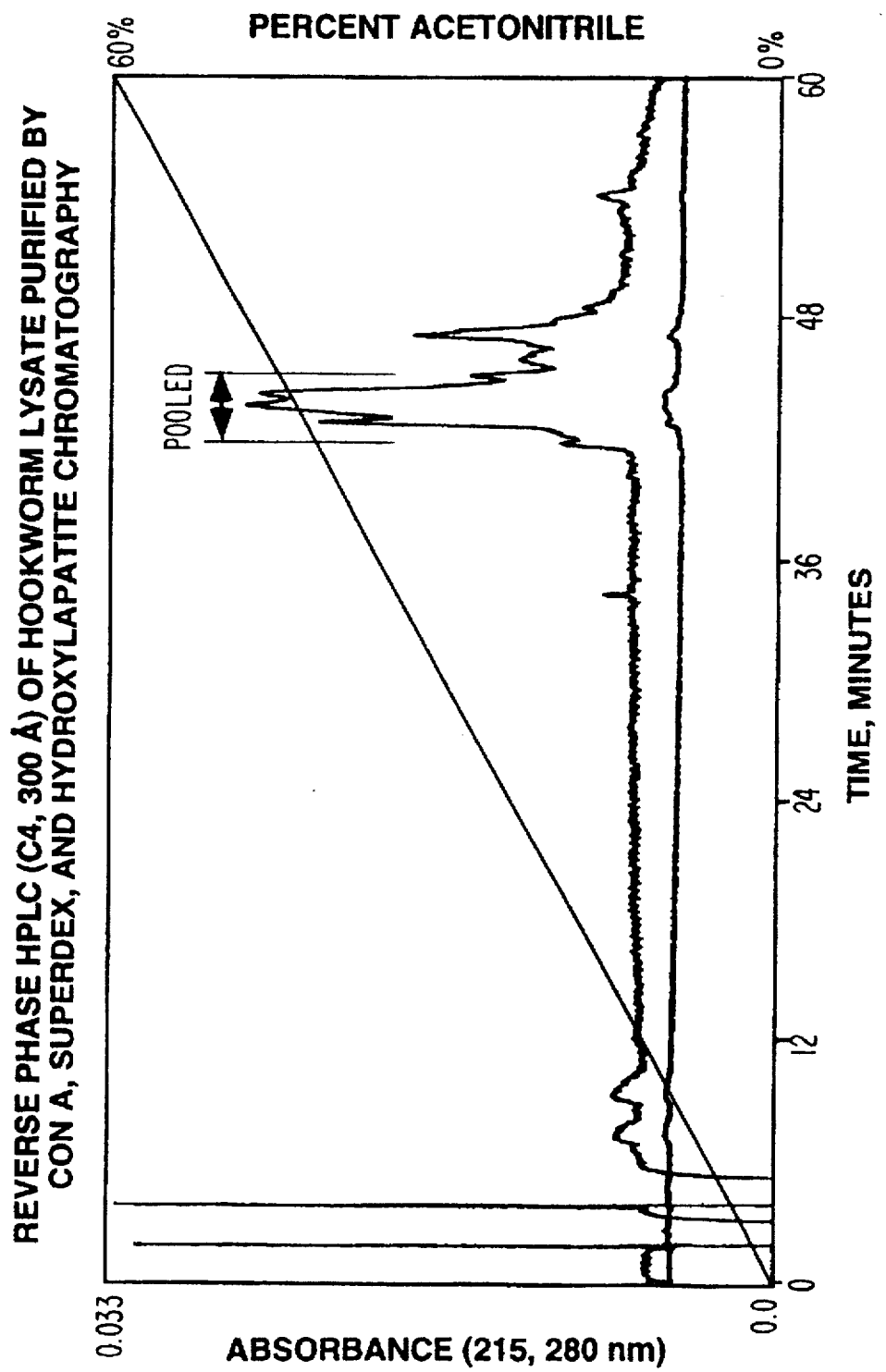
FIG. 4 depicts a chromatogram from reverse phase HPLC of Ancylostoma lysate isolated by Concanavalin A Sepharose, Superdex 200 and hydroxyapatite chromatography as described in Example 1(E).

FIG. 4 depicts the results of reverse phase HPLC of the Neutrophil Inhibitory Factor. Inhibitory activity eluted between 43 and 45% acetonitrile, the activity corresponding with a broad peak at 43–45 minutes.

TABLE I

SUMMARY OF EXAMPLE PURIFICATION

| FRACTIONATION STEP | PROTEIN (mg) | PERCENT ACTIVITY | SPECIFIC ACTIVITY | FOLD PURIF. |
|---|---|---|---|---|
| EXTRACTION | 528 | 100 | 0.2 | 1 |
| ConA ELUATE | 21.7 | 38 | 1.8 | 9 |
| SUPERDEX POOL | 1.5 | 25 | 16.7 | 88 |
| HYDROXYAPATITE POOL | 0.3 | 12 | 40.0 | 200 |

EXAMPLE 2

ISOLATION OF THE NEUTROPHIL ADHESION INHIBITOR FACTOR FROM ANCYLOSTOMA LYSATE USING PREPARATIVE ISOELECTRIC FOCUSING

Hookworm lysate was partially fractionated and desalted by molecular sieve chromatography on a 2.6 cm×60 cm column of Superdex 200 prep (Pharmacia) attached in series with an identical column (combined dimensions of 2.6×120 cm). Both columns were pre-equilibrated with 0.01M sodium phosphate, pH 7.00, 10% (v/v) glycerol at 24° C. Adhesion inhibiting fractions eluting at 350–370 ml were diluted to 55 ml by the addition of 1.4 ml of 40% Biolyte 3–10 ampholyte (BioRad) and 10% (v/v) glycerol. This mixture was focused with a constant power of 12 W for 5 hours at 4° C. in a Rotofor preparative isoelectric focusing prep cell (BioRad). Twenty fractions were harvested; inhibitory activity was detected in fractions 6–9, corresponding to an isoelectric point of 4.5. The overall yield of inhibitory activity for this step was approximately 30%.

EXAMPLE 3

ION EXCHANGE CHROMATOGRAPHY

Hookworm lysate fractionated by molecular sieve chromatography on Superdex 75 (Pharmacia) was mixed with an equal volume of Mono Q buffer [0.02M Tris-HCl, pH 7.5] and loaded on to a 0.5×5.0 cm Mono Q anion exchange column (Pharmacia) equilibrated with Mono Q buffer at a flow rate of 1 ml/minute (306 cm/hour). The column was then developed with a linear gradient of 0–0.5M NaCl in column buffer at 0.5 ml/minute (153 cm/hour). Neutrophil inhibitory activity consistently eluted at 0.4M NaCl. The overall yield of inhibitory activity for this isolation was low (about 2–5%).

EXAMPLE 4

SDS-POLYACRYLAMIDE GEL ELECTROPHORESIS

The protein composition of hookworm lysate and fractionated lysate was analyzed by sodium dodecyl sulfate polyacrylamide gel electrophoresis (SDS-PAGE) (Laemmli, U.K. 1970, Nature 227, 680) after silver staining (Morrisey, J. H. 1981, Anal. Biochem. 117, 307). Samples were mixed with an equal volume of 20% glycerol, 5% SDS, and 0.125M Tris-HCl, pH 6.8 and placed in a boiling water bath for 5 minutes. Samples were subsequently applied onto 10% SDS polyacrylamide slab gels of 0.75 mm thickness and subjected to electrophoresis for 2 hours at constant voltage (125 V).

Figure 5:
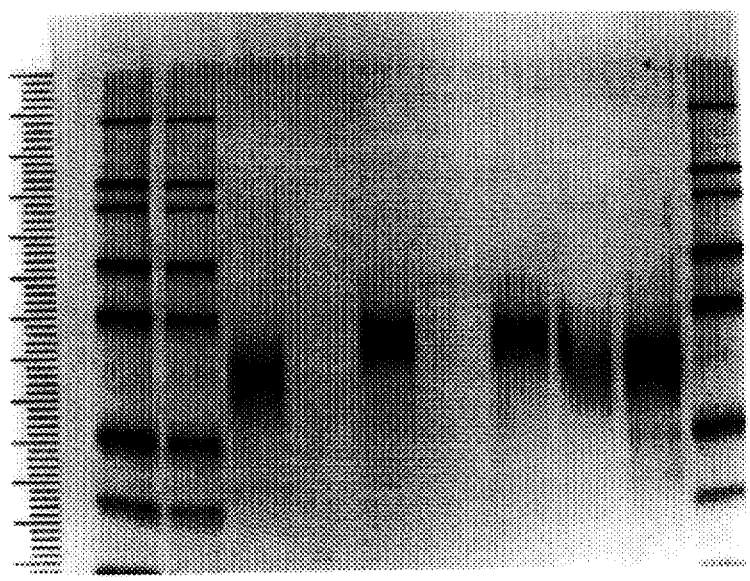
FIG. 5 depicts a gel pattern run using SDS-gel electrophoresis of the HPLC isolate and certain molecular weight standards.

FIG. 5 depicts the results of SDS polyacrylamide gel electrophoresis. Samples were applied to a 10% polyacrylamide slab gel (Novex, La Jolla, Calif.). Lanes 1–10, left to right, are (1) molecular weight standards; (2) molecular weight standards; (3) HPLC pool of HA fractions #37–41, non-reduced; (4) blank; (5) HPLC pool of HA fractions #37–41, reduced; (6) blank, (7) HPLC pool of HA fractions #37–41, reduced, (8) HPLC pool of HA fractions #37–41, non-reduced; (9) HPLC pool of HA trailing fractions #42–48, non-reduced, (10) molecular weight standards. The molecular weight standards used were: myosin, 200,000 (rabbit muscle); beta-galactosidase, 116,300 (*E. coli*); phosphorylase b, 97,400 (rabbit muscle); bovine serum albumin, 66,300; glutamic dehydrogenase, 55,400, (bovine liver); carbonic anhydrase, 31,000, (bovine erythrocyte); trypsin inhibitor, 21,500, (soybean).

Following the last step of the isolation procedure (reverse phase HPLC) only a single diffuse band with an apparent molecular weight ranging from 33,000 to 47,000 was observed upon SDS-PAGE (see FIG. 5). When 50 mM dithiothreitol was added to the sample prior to boiling, the diffuse band migrated with an estimated molecular weight of 43,000 to 54,000.

EXAMPLE 5

LASER-DESORPTION TIME-OF-FLIGHT MASS SPECTROMETRY OF THE ISOLATED NEUTROPHIL ADHESION INHIBITOR

The estimated mass for the Neutrophil Inhibitory Factor isolated as described in Example 1(E) was determined using laser-desorption time-of-flight mass spectrometry.

A 1 µl aliquot of the sample was diluted with an equal voume of a saturated solution of 3,5-dimethoxy-4-hydroxycinnamic acid dissolved in 30% aqueous $CH_3CN$, 0.1% TFA. The diluted sample was spotted onto a copper sample stage and allowed to air dry. Mass analysis was performed using a Shimadzu LAMS-50KS laser desorption time of flight mass spectrometer (Shimadzu Corp., Kyoto, Japan). Ionization of the sample was accomplished by focusing 500 laser pulses (355 nm, pulse width <5 nsec) from a Nd-YAG laser (Spectra-Physics, Inc., Mt. View, Calif.) onto the sample stage. The resulting ions were accelerated into the mass spectrometer by a 5 kV potential. Calibration of the instrument was accomplished using standard proteins of known mass.

Figure 6:
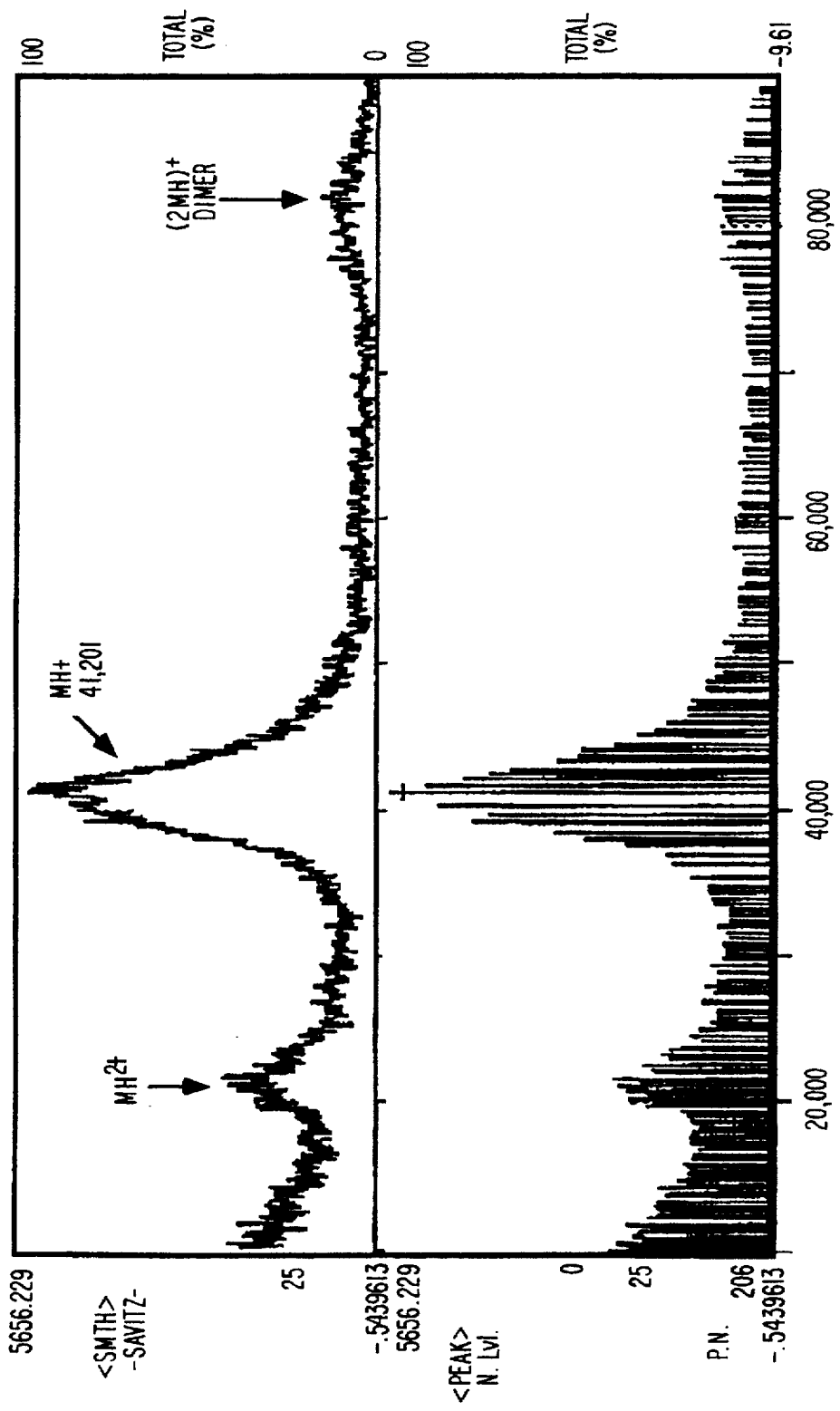
FIG. 6 depicts laser-desorption time-of-flight mass spectrometry of the purified Neutrophil Inhibitory Factor of the present invention.

FIG. 6 depicts the results of laser-desorption time-of-flight mass spectrometry of the isolated neutrophil adhesion inhibitor. Five picomoles of the purified neutrophil function inhibitor was analyzed with a laser desorption time-of-flight mass spectrometer. The estimated mass was determined as 41,200. A small fraction of the sample had a mass of 82,400; this was interpreted to be a dimer.

EXAMPLE 6

NEUTROPHIL ADHESION INHIBITOR IS A GLYCOPROTEIN

Purified neutrophil function inhibitor (~2 µg) was electrophoresed in a 10% SDS polyacrylamide gel and the resolved protein transferred by Western blotting (Towbin, et al., 1979 Proc. Natl. Acad. Sci. (U.S.A.) 76, 4350–4354) to a Zeta-Probe® nitrocellulose membrane (BioRad, Emeryville, Calif.). The membrane was treated as described in the instructions to the GlycoTrack™ Kit (Oxford GlycoSystems, Rosedale, N.Y.) to oxidize carbohydrates to aldehydes which were then reacted with biotin-hydrazide leading to incorporation of biotin into any carbohydrate present. Biotinylated carbohydrate was subsequently detected by reaction with a streptavidin-alkaline phosphatase conjugate. Visualization was achieved using a substrate which reacts with alkaline phosphatase bound to glycoproteins on the membrane, forming a colored precipitate. Neutrophil Inhibitory Factor was stained using this method, demonstrating that it contained carbohydrate and is therefore a glycoprotein.

EXAMPLE 7

ORGANIC EXTRACTION OF THE HOOKWORM LYSATE

One milliliter of hookworm homogenate known to have inhibitory activity in the neutrophil-plastic adhesion assay was extracted by vortexing 1 minute with 1 ml of a chloroform/methanol (2:1) mixture in a 15 ml glass Corex test tube. The organic layer was removed and dried under a stream of nitrogen gas. Residual lipids were resuspended in 0.5 ml HSA assay buffer by sonication for 2 minutes (Branson Model 1200, Danbury, Conn.). Resuspended lipids had no inhibitory activity in the neutrophil-plastic adhesion assay when tested at a final dilution of 1:2.

EXAMPLE 8

ISOLATION OF cDNA ENCODING THE NEUTROPHIL FUNCTION INHIBITOR FROM HOOKWORM (A) Cloning by Nucleic Acid Hybridization Total RNA is prepared from hookworms by guanidinium thiocyanate extraction (McDonald et al., 1987 *Methods Enzymol.* 152, 219–227). Messenger RNA (mRNA) is purified from approximately 2 mg total hookworm RNA using messenger affinity paper (MAP; Amersham, Arlington Heights, Ill.) following directions specified by the manufacturer (Amersham, Arlington Heights, Ill.). Double-stranded complementary DNA (cDNA) is synthesized from approximately 5 µg hookworm mRNA using avian myoblastosis virus reverse transcriptase with random hexamer primers, following directions specified by the manufacturer (Amersham). cDNA fragments are ligated to EcoRI linkers (Stratagene, La Jolla, Calif.) and linkered cDNA fragments are separated from unligated linkers on a 5% polyacrylamide gel. Linkered hookworm cDNA is ligated to bacteriophage λgt10 arms (Stratagene) with Gigapack Gold II following directions specified by the manufacturer (Stratagene). Approximately 2×10E6 recombinant bacteriophage from this hookworm cDNA library are screened with at least one $^{32}$P-labelled oligonucleotide that corresponds to amino acid sequence obtained from the purified hookworm Neutrophil Inhibitory Factor. For these oligonucleotide probes, it is preferable to use an amino acid sequence that contains at least 15 contiguous amino acid residues. To increase the efficiency of screening this hookworm cDNA library, at least two probes that are derived from distinct amino acid sequence of the neutrophil inhibitory factor are used in parallel screening experiments. Codon usage for the hookworm inhibitory factor oligonucleotide probes is according to the preferred codons found for other invertebrate organisms, preferably parasitic worms. Prehybridization and hybridization conditions are 5× SSC (SSC: 150 mM NaCl 15 mM trisodium citrate), 0.05M sodium phosphate, pH 6.8, 5× Denhardt's solution (Sigma), 10% dextran sulfate, 20 µg/ml boiled sheared salmon sperm DNA (Stratagene, La Jolla, Calif.) at 42° C. with 20% formamide. Filters are washed for 30 min with 2× SSC at 45° C. cDNA inserts from bacteriophage that hybridize to the hookworm Neutrophil Inhibitory Factor oligonucleotide probes are subcloned into an appropriate vector and their nucleotide sequence determined using dideoxy sequencing (Sanger et al., 1977 Proc. Natl. Acad. Sci. (U.S.A.) 74, 5463–5467).

(B) Cloning by Expression in λgt11

Polyclonal and monoclonal antibodies to the hookworm Neutrophil Inhibitory Factor are generated by immunizing rabbits and mice, respectively, with purified Neutrophil Inhibitory Factor. For polyclonal antibodies, approximately 20 µg of the Neutrophil Inhibitory Factor is suspended in Freund's complete adjuvant and administered to rabbits by subcutaneous injection. Immunized rabbits are boosted with an equivalent quantity of antigen at three week intervals, and serum is tested for antibody specific to the Neutrophil Inhibitory Factor at weekly intervals beginning two months after the initial immunization. For monoclonal antibodies, mice are immunized with 10 µg of the purified hookworm Neutrophil Inhibitory Factor in completed Freund's adjuvant, by subcutaneous injection. Hybridomas are prepared from immunized mice by established procedures (Harlow and Lane, 1988 in *Antibodies. A Laboratory Manual* [Cold Spring Harbor Laboratory Press, Cold Spring Harbor N.Y.] pp. 139–243). To screen for polyclonal and monoclonal antibodies that recognize the inhibitory factor, an antigen capture assay (Harlow and Lane, 1988) is used.

A hookworm cDNA expression library is constructed as described for the section on cloning by hybridization except the cDNA is ligated into EcoRI-digested λAgt11 arms (Stratagene). 2×10E6 recombinants will be screened by transferring fusion proteins synthesized by recombinant bacteriophage to nitrocellulose filters and probing with antibodies, either polyclonal or monoclonal, directed toward hookworm Neutrophil Inhibitory Factor. The synthesis of fusion proteins by recombinant bacteriophage is induced by growing the bacteriophage at 42° C. for 4 hours in the *E. coli* strain Y1090hsdR (Jendrisak et al., 1987 *Methods Enzymol.* 152, 359). Bacteriophage are shifted to 37° C. and overlaid with a sterile nitrocellulose filter impregnated with isopropylthio-β-D-galactoside (Sigma, St. Louis, Mo.), and filters are screened with antibodies toward the hookworm Neutrophil Inhibitory Factor. cDNA inserts from bacteriophage that bind antibodies to the hookworm Neutrophil Inhibitory Factor are subcloned into an appropriate vector and their nucleotide sequence determined using dideoxy sequencing (Sanger et al., 1977 Proc. Natl. Acad. Sci. (U.S.A.) 74, 5463–5467).

(C) Cloning by Expression in Mammalian Cells

Hookworm cDNA is prepared as described in the section on cloning by hybridization. This method may employ the plasmid vector pcDM8 which is specifically designed for expression of proteins in mammalian cells. This vector contains both bacterial and mammalian origins of replication in addition to a mammalian promoter that is adjacent to a multiple cloning site (Aruffo and Seed, 1987). To increase the probability that recombinants will contain sequence that encodes a full length polypeptide the technique of G/C tailing may be used to join the cDNA to the vector. The technique of G/C tailing is described in detail elsewhere (Kriegler, 1991 in *Gene Transfer and Expression. A Laboratory Manual.* [W. H. Freeman and Co., New York, N.Y.] pp. 114–135). Recombinant plasmids may be used initially to transform *E. coli*, and the library (approximately 1×10E6 recombinants) divided into pools of 1000 colonies for screening. Plasmid DNA prepared from these pools can be used to transfect COS-7 cells. (ATCC CRL 1651). Tissue culture supernatant from dishes that contain transfected mammalian cells are assayed for inhibitory activity in the neutrophil-plastic adhesion assay described above. Supernatants that test positive in this assay may be confirmed using the neutrophil-HUVEC adhesion assay (see Example A). The original bacterial plates representing tissue culture supernatant pools that test positive in the neutrophil-HUVEC assay (see Example A) are organized into a grid of bacterial colonies, approximately 33×33 for a pool of 999 colonies. Plasmid DNA is prepared from the 33 clones in each row and column of the grid (i.e., 66 preparations), and this DNA used to transfect C057 cells. The clone that expresses neutrophil inhibitory activity can be unambiguously identified by testing supernatants from these transfectants in the neutrophil assays as before (See Example A). cDNA inserts from plasmids that express inhibitory activity in the neutrophil-HUVEC adhesion assay are subcloned into an appropriate vector and their nucleotide sequence determined using dideoxy sequencing (Sanger et al., 1977 Proc. Natl. Acad. Sci. (U.S.A.) 74, 5463–5467).

EXAMPLE A

ASSAYS OF NEUTROPHIL INHIBITORY ACTIVITY

The Neutrophil Inhibitory Factor of the present invention demonstrated activity in inhibiting neutrophil activity as measured by neutrophil-HUVEC and neutrophil-plastic adhesion assays, homotypic neutrophil aggregation assay and hydrogen peroxide release assay. This inhibitory factor was isolated from hookworm tissue lysates as an enriched composition by a variety of methods including gel filtration chromatography, chromatography on hydroxyapatite and concanavalin A sepharose, C4 reverse-phase HPLC, Mono-Q ion exchange chromatography and preparative isoelectric focusing. The isolated factor appears to inhibit neutrophil adhesion to endothelial cell monolayers by inhibiting neutrophil activation.

(A) Cells and Reagents

Primary human umbilical vein endothelial cells (HUVEC), obtained from Clonetics (San Diego, Calif.), were maintained in EGM-UV medium (Clonetics) with 15% fetal bovine serum (FBS), in a 5% $CO_2$ atmosphere. HUVEC were passaged twice and used to seed fibronectin-coated 96 well microtiter plates (Collaborative Research, Bedford, Mass.) for adhesion assays.

The protease inhibitors E64, pepstatin A, chymostatin and APMSF were obtained from Calbiochem (La Jolla, Calif.).

Neutrophils were isolated using Mono-Poly resolving medium (ICN Biomedicals, Costa Mesa, Calif.) from either heparinized or citrated human blood following the instructions of the manufacturer. Neutrophils were resuspended in HSA buffer (RPMI1640 with 10 mM HEPES pH 7.4, 1.2 mM CaCl, 1.0 mM MgCl, 1% human serum albumin) at a concentration of 6.6×10E6 cells/ml and used within one hour after isolation.

Neutrophils were fluorescently labelled by the following procedure. The cells were washed once in Hank's balanced salt solution (HBSS) and resuspended at 1×10E7 cells/ml in HBSS containing 20 µg/ml calcein (Molecular Probes; Eugene, Oreg.). The calcein was initially solubilized in 50 µl dry dimethylsulfoxide prior to its addition to the HBSS. Cells were incubated at 37° C. with occasional mixing by inversion. After 45 minutes incubation the cells were chilled on ice for 5 minutes and then washed twice with ice-cold HSA buffer. Labelled neutrophils were resuspended in HSA buffer at 1.3×10E7 cells/ml for use in adhesion assays.

(B) Neutrophil-HUVEC Adhesion Assays

Calcein-labelled neutrophils (175 µl at 1.32×10E7 cells/ml) were preincubated for 10 minutes at room temperature with 175 µl of test fraction (diluted in HSA buffer) in the presence of 160 nM phorbol 12-myristate 13-acetate (PMA; Sigma, St. Louis, Mo.). A 96 well plate was used for this assay. One hundred microliters of this suspension was then aliquoted into each of three replicate wells that contained HUVEC monolayers. Neutrophils were incubated with the HUVEC monolayer for 30 minutes at 37° C. To remove non-adherent cells, wells were first filled with 250 µl HSA buffer, sealed with parafilm and then centrifuged inverted for 3 minutes at 75×g. Inverted plates were then placed on a rocking platform shaker for 5 minutes, after which contents were decanted off and wells were washed twice with 100 µl HSA buffer. Adherent neutrophils were lysed in 100 µl 0.1% (v/v) Triton X-100 (in 50 mM Tris HCl pH 7.4), and agitated for 10 minutes on a plate shaker. Twenty five microliters of the neutrophil/endothelial cell lysate were transferred to a 96 well microtiter plate that contained 100 µl of 50 mM Tris pH 7.4, and the wells were read at 530 nm (485 nm excitation) on a Cytofluor fluorometric plate reader (Millipore; Bedford, Mass.).

The hydroxyapatite pool preparation of hookworm Neutrophil Inhibitory Factor (see Example 1(D)) inhibited neutrophil adhesion to HUVEC monolayers with an $IC_{50}$ of about 10 nM.

(C) Neutrophil-Plastic Adhesion Assay

Neutrophils (20 µl at 6.6×10E6/ml) were incubated with 5 µl PMA (0.8 µM) for 5 minutes at room temperature in a 0.5 ml polypropylene test tube. Twenty microliters of test fraction, diluted in HSA buffer, were added and the suspension was mixed gently. Aliquots of 10 µl of this suspension were added in triplicate to microtiter wells of 60-well HCA (Terasaki) plates (Nunc, Naperville, Ill.). Neutrophils were incubated 5 minutes at 37° C. and non-adherent cells were removed by submerging the plate 6 times in HBSS. Adherent neutrophils were quantitated by counting under an inverted light microscope.

Binding was quantitated visually. PMA-activated neutrophils spread and adhere tightly to polystyrene plastic. Non-activated neutrophils (i.e., in the absence of PMA) remain round and translucent and do not adhere tightly to plastic. Adherent neutrophils were larger, rhomboid in shape and more opaque, with a granular appearance. In the absence of Neutrophil Inhibitory Factor, greater than 80% of PMA-activated neutrophils rapidly and irreversibly bound plastic, underwent shape change and were not removed by the gentle wash procedure. Moreover, fractions containing the Ancylostoma Neutrophil Inhibitory Factor exhibited a profound inhibitory effect on plastic binding by activated neutrophils.

The hydroxyapatite pool preparation of hookworm Neutrophil Inhibitory Factor (see Example 1(D)) inhibited neutrophil adhesion to plastic in this assay with an $IC_{50}$ of about 10 nM.

(D) Homotypic Neutrophil Aggregation

Neutrophil aggregation was performed at 37° C. in a Scienco dual channel aggregometer (Morrison, CO). Neutrophils (190 µl at 6.6×10E6/ml) were preincubated with 200 µl test fraction (diluted in HSA Buffer) in a glass cuvette (Scienco) for 2 minutes at room temperature. Ten microliters of PMA were added to initiate aggregation (80 nM final). The inhibition of neutrophil aggregation was measured at the maximum aggregation response 5 minutes after the addition of PMA.

The hydroxyapatite pool preparation of Neutrophil Inhibitory Factor (see Example 1(D)) inhibited neutrophil adhesion with an $IC_{50}$ of about 10 nM.

(E) Hydrogen Peroxide Release Assay

Neutrophils (6.6×10E6 cells/ml) were incubated with test fractions in Release Assay Buffer (HBSS with 25 mM glucose, 10% FBS, 200 µg/ml phenol red, 32 µg/ml horseradish peroxidase) for 5 minutes at 37° C. Incubation vessels consisted of 1.5 ml plastic test tubes that were precoated with HBSS containing 50% FBS at 37° C. for 60 minutes; coated tubes were washed twice with 0.15M NaCl before use. FMLP (Sigma; St. Louis, Mo.) at a final concentration of 250 µM was added and the neutrophil/test compound suspension was incubated at 37° C. for 60 minutes. Cells were pelleted by centrifugation at 8000×g for 3 minutes and 200 µl of supernatant was transferred to a 96 well microtiter plate. Ten microliters of 1N NaOH was added to each well and absorbance was read at 610 nm with a Molecular Devices ThermoMax plate reader. Hydrogen peroxide concentrations were determined by using a standard curve. Data points were done in duplicate.

The hydroxyapatite pool preparation of hookworm Neutrophil Inhibitory Factor inhibited hydrogen peroxide release from neutrophils with an $IC_{50}$ of about 10 nM.

EXAMPLE B

DETERMINATION OF SPECIFICITY OF THE NEUTROPHIL ADHESION INHIBITOR

To test the specificity of the Neutrophil Inhibitory Factor of the present invention, and to confirm that it did not inhibit neutrophil activation by a general cytotoxic mechanism, the activity of the inhibitor was assessed in a non-neutrophil cell adhesion-based assay, platelet aggregation.

The effects of the hookworm Neutrophil Inhibitory Factor on blood platelet aggregation were examined. Platelet aggregation was performed with human platelet-rich plasma (PRP). PRP was stirred at 37° C. in an aggregometer (Scienco Model 247, Morrison, CO) and aggregation was initiated by the addition of 10 µM ADP (Sigma, St. Louis, Mo.). Aggregation was monitored as a change in light transmittance, and is expressed as the initial rate of aggregation. A concentration of Neutrophil Inhibitory Factor of approximately 150 nM, a concentration that completely blocked neutrophil function as assessed by neutrophil-HUVEC and neutrophil-plastic adhesion assays, homotypic neutrophil aggregation and hydrogen peroxide release by neutrophils, had no inhibitory effect on ADP-induced aggregation of human platelets.

We claim:

1. A glycoprotein isolated from Ancylostoma canium which has an apparent molecular weight of about 38,000 to 44,000 Daltons as determined by laser-desorption time-of-flight mass-spectrometry; and an isoelectric point of about 4.5 as determined by preparative isoelectric focusing and which has neutrophil inhibitory activity.

2. A glycoprotein according to claim 1 which was isolated from a homogenate of Ancylostoma caninum using chromatography on Concanavalin-A, gel filtration chromatography using a gel filtration medium comprising a matrix of cross-linked agarose and dextran having a separation range of 10 to 600 KD, chromatography on hydroxyapatite and C4 reverse phase HPLC.

3. A method of preparing a composition enriched for Neutrophil Inhibitory Factor from a homogenate of a parasitic worm of the genus Ancylostoma that has neutrophil inhibitory activity which comprises (a) subjecting the homogenate to chromatography on Concanavalin-A, (b) subjecting the material having neutrophil inhibitory activity from step (a) to chromatography on gel filtration media comprising a matrix of cross-linked agarose and dextran having a separation range of 10 to 600 KD, and (c) subjecting the material having neutrophil inhibitory activity from step (b) to column chromatography on hydroxyapatite.

4. A method according to claim 3 further comprising (d) subjecting the material having neutrophil inhibitory activity from step (c) to reverse phase HPLC using a C4 column.

* * * * *

UNITED STATES PATENT AND TRADEMARK OFFICE
CERTIFICATE OF CORRECTION

PATENT NO. : 5,708,141
DATED : January 13, 1998
INVENTOR(S) : Matthew Moyle, David L. Foster and George P. Vlasuk It is certified that error appears in the above-identified patent and that said Letters Patent is hereby corrected as shown below:

Title page,
Item [57], ABSTRACT, please change to:
-- Compositions enriched for Neutrophil Inhibitory Factor which inhibit neutrophil activity including adhesion to vascular endothelial cells are provided. Such compositions may comprise a glycoprotein isolated from nematodes. These compositions are useful in the therapy of conditions which involve abnormal or undesired inflammatory responses. --

Signed and Sealed this

Twentieth Day of July, 2004

JON W. DUDAS
*Acting Director of the United States Patent and Trademark Office*